(12) United States Patent
Yamaguchi et al.

(10) Patent No.: US 8,822,251 B2
(45) Date of Patent: Sep. 2, 2014

(54) MICRO ELECTRO MECHANICAL SYSTEM, SEMICONDUCTOR DEVICE, AND MANUFACTURING METHOD THEREOF

(75) Inventors: Mayumi Yamaguchi, Kanagawa (JP); Konami Izumi, Kanagawa (JP); Fuminori Tateishi, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 12/426,602

(22) Filed: Apr. 20, 2009

(65) Prior Publication Data

US 2009/0230815 A1    Sep. 17, 2009

Related U.S. Application Data

(62) Division of application No. 11/549,310, filed on Oct. 13, 2006, now Pat. No. 7,528,529.

(30) Foreign Application Priority Data

Oct. 17, 2005    (JP) ................................. 2005-302343

(51) Int. Cl.
*H01L 21/00* (2006.01)
*H01L 21/30* (2006.01)
*H01L 21/46* (2006.01)

(52) U.S. Cl.
USPC .............................. 438/48; 438/109; 438/456

(58) Field of Classification Search
USPC ............................................ 438/48–98, 458
See application file for complete search history.

(56) References Cited

U.S. PATENT DOCUMENTS

| | | | |
|---|---|---|---|
| 5,818,145 A | 10/1998 | Fukiharu | |
| 6,204,593 B1 | 3/2001 | Takahashi | |
| 6,276,781 B1 | 8/2001 | Hasegawa | |
| 7,067,926 B2 | 6/2006 | Yamazaki et al. | |
| 7,157,836 B2 | 1/2007 | Kinoshita | |
| 7,511,380 B2 | 3/2009 | Yamazaki et al. | |
| 2001/0004180 A1 | 6/2001 | Kishimoto | |
| 2002/0084858 A1 | 7/2002 | Luff | |

(Continued)

FOREIGN PATENT DOCUMENTS

| | | |
|---|---|---|
| CN | 1519929 A | 8/2004 |
| EP | 1432032 A2 | 6/2004 |

(Continued)

OTHER PUBLICATIONS

Khalil NAJAFI; "Micropackaging Technologies for Integrated Microsystems: Application to MEMS and MOEMS"; Proceedings of SPIE; 2003; pp. 1-19, vol. 4979.

(Continued)

*Primary Examiner* — Calvin Choi
(74) *Attorney, Agent, or Firm* — Fish & Richardson P.C.

(57) ABSTRACT

The present invention provides a MEMS and a sensor having the MEMS which can be formed without a process of etching a sacrifice layer. The MEMS and the sensor having the MEMS are formed by forming an interspace using a spacer layer. In the MEMS in which an interspace is formed using a spacer layer, a process for forming a sacrifice layer and an etching process of the sacrifice layer are not required. As a result, there is no restriction on the etching time, and thus the yield can be improved.

19 Claims, 14 Drawing Sheets

(56) References Cited

U.S. PATENT DOCUMENTS

| | | |
|---|---|---|
| 2003/0020062 A1* | 1/2003 | Faris ............................... 257/40 |
| 2003/0047280 A1* | 3/2003 | Takayama et al. ............ 156/344 |
| 2003/0058069 A1 | 3/2003 | Schwartz |
| 2003/0093895 A1* | 5/2003 | Miyazaki et al. ................ 29/622 |
| 2003/0155845 A1 | 8/2003 | Uchiyama |
| 2004/0056587 A1* | 3/2004 | Kim ............................... 313/500 |
| 2004/0056742 A1 | 3/2004 | Dabbaj |
| 2004/0157364 A1* | 8/2004 | Combi et al. ................. 438/106 |
| 2004/0159960 A1 | 8/2004 | Fujiwara |
| 2005/0192129 A1 | 9/2005 | Kuwabara |
| 2005/0218488 A1* | 10/2005 | Matsuo ........................ 257/678 |
| 2005/0282306 A1* | 12/2005 | Yamanaka ...................... 438/57 |
| 2006/0138908 A1 | 6/2006 | Iwase |

FOREIGN PATENT DOCUMENTS

| | | |
|---|---|---|
| EP | 1 445 861 A2 | 8/2004 |
| JP | 06-188670 A | 7/1994 |
| JP | 11-078003 A | 3/1999 |
| JP | 11-174994 | 7/1999 |
| JP | 2000-058866 | 2/2000 |
| JP | 2000-208018 | 7/2000 |
| JP | 2003-087084 A | 3/2003 |
| JP | 2003-218662 A | 7/2003 |
| JP | 2003-258583 A | 9/2003 |
| JP | 2004-214469 | 7/2004 |
| JP | 2004-243462 | 9/2004 |
| JP | 2005-270640 A | 10/2005 |
| KR | 2003-095035 | 12/2003 |

OTHER PUBLICATIONS

Chinese Office Action (Application No. 200610163587.3), Dated Aug. 9, 2010 with English Translation.

* cited by examiner

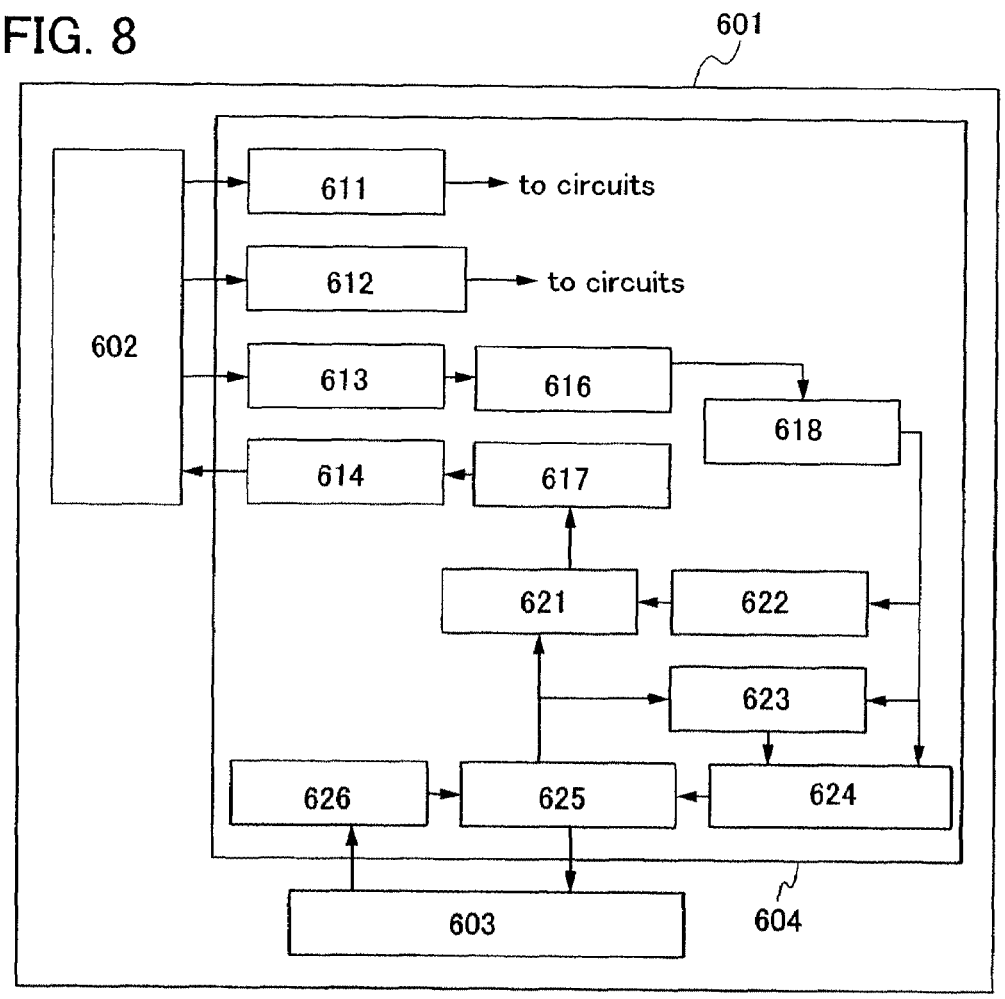

380

MICRO ELECTRO MECHANICAL SYSTEM, SEMICONDUCTOR DEVICE, AND MANUFACTURING METHOD THEREOF

CROSS-REFERENCE TO RELATED APPLICATIONS

This application is a divisional of U.S. application Ser. No. 11/549,310, filed Oct. 13, 2006, now allowed, which claims the benefit of a foreign priority application filed in Japan as Serial No. 2005-302343 on Oct. 17, 2005, both of which are incorporated by reference.

BACKGROUND OF THE INVENTION

1. Field of the Invention

The present invention relates to a semiconductor device having a minute structure body and a manufacturing method thereof.

2. Description of the Related Art

MEMS (micro electro mechanical system) technology which is applied for electronic parts such as a filter, sensors or actuators has been developed.

MEMS is formed using a silicon wafer, has a structure layer forming an interspace, and includes an etching process of a sacrifice layer of the silicon wafer so as to form the interspace. The etching process of a sacrifice layer is a process for forming an opening in the lateral direction to form an interspace, not a process for an opening in the vertical direction as conducted in a manufacturing process of a semiconductor integrated circuit.

As just described above, MEMS has a feature that a substrate is processed three-dimensionally and is essentially different from a manufacturing process of a semiconductor integrated circuit in which a circuit pattern is formed two-dimensionally. Thus, the etching process in manufacturing MEMS takes time and yield is poor, since a form to be processed by the etching is complicated.

For example, in order to shorten the time needed for etching a sacrifice layer, a tunnel structure is formed inside the sacrifice layer by providing the sacrifice layer in two-layer form, and thus, an etching solution goes into the sacrifice layer fast through the tunnel structure at the time of etching of the sacrifice layer (for example, Reference 1: Japanese Published Patent Application No. 2000-58866).

SUMMARY OF THE INVENTION

However, in the case of the sacrifice layer in two-layer form, the etching process is inevitable and it is difficult to simplify and shorten the manufacturing process. In addition, it has thus been difficult to improve the manufacturing yield.

The present invention has been made in view of the above problems. It is an object of the present invention to provide an easy manufacturing method of a micro electro mechanical system and a semiconductor device including the micro electro mechanical system.

In accordance with the present invention, in a micro electro mechanical system having an interspace and a semiconductor device including the micro electro mechanical system and an electric circuit, an interspace to secure a work area of the micro electro mechanical system is formed using a spacer layer having adhesiveness which is formed selectively between a substrate and a functional layer. Specifically, a MEMS (also referred to as a micro electro mechanical system) in which an interspace is formed using a spacer layer is formed in accordance with the present invention. A device including the micro electro mechanical system like this and an electric circuit is referred to as a semiconductor device. Such an electric circuit is mainly formed from a semiconductor element and the like, and the semiconductor device can have a structure enabling wireless communication.

Hereinafter, the specific structure examples of the present invention are shown.

One mode of a micro electro mechanical system of the present invention is that a first spacer layer, a layer including a piezoelectric element, a second spacer layer and a second film substrate are formed over a first film substrate. Here, the layer including the piezoelectric element includes the piezoelectric element formed by stacking a first electrode, a piezoelectric material and a second electrode. The number of the piezoelectric elements included in the layer including the piezoelectric element may be one or more. The first spacer layer and the second spacer layer are selectively formed using materials having adhesiveness so as to form an opening portion to be overlapped with the piezoelectric element provided in the layer including the piezoelectric element.

In addition, the area of the opening portion is larger than the area of the piezoelectric material forming the piezoelectric element, specifically, the distance between an end of the piezoelectric material and an end of the opening is preferably 10 μm or more and 100 μm or less. Further, the first spacer layer and the second spacer layer may have forms to be considered to be similar (or about the same form), and may be stacked over a region to be considered to be similar (or about the same region). Therefore, the plural interspaces can be disposed to be overlapped.

Another mode of a micro electro mechanical system of the present invention is that a first spacer layer, a functional layer, a second spacer layer and a second film substrate are formed over a first film substrate. Here, the functional layer can be applied to not only a piezoelectric element but also particular functional elements which can be formed by stacking thin films, for example, a passive element and an active element such as a semiconductor element, a thermoelectric element, a strain resistor element, an inductor and a capacitor. The number of particular functional elements included in the layer may be one or more, and further, one kind or plural kinds of particular functional elements may be used. As in the above mode, the first spacer layer and the second spacer layer are selectively formed using materials having adhesiveness so as to have an opening portion in a particular portion. Specifically, in the particular portion, the opening portion is provided to be overlapped with the particular functional element provided in the layer including the particular functional element or with an electrode electrically connected to the particular functional element.

Further, it is preferable that the first spacer layer and the second spacer layer have a form to be considered to be similar (or the same form), and be stacked over a region to be considered to be similar (or the same region). Therefore, a plurality of interspaces can be disposed to be overlapped.

Next, one mode of a manufacturing method of a micro electro mechanical system of the present invention is that a peeling layer, a layer including a piezoelectric element, and a first spacer layer are formed over a substrate, and a first film substrate is attached thereonto. By utilizing the attachment of the layer including a piezoelectric element to the first film substrate by the adhesiveness of the first spacer layer, the layer including a piezoelectric element is peeled from the substrate and transferred to the first film substrate. After that, the second film substrate in which the second spacer layer is selectively formed is attached to the side of the layer including a piezoelectric element with which the substrate has been in contact.

Another mode of a manufacturing method of a micro electro mechanical system of the present invention is that a peeling layer, a functional layer including a particular functional element, and a first spacer layer are formed over a substrate, and a first film substrate is attached thereonto. By utilizing the attachment of the functional layer to the first film substrate by the adhesiveness of the first spacer layer, the functional layer is peeled from the substrate and transferred to the first film substrate. After that, the second film substrate in which the second spacer layer is selectively formed is attached to the side of the functional layer substrate with which the substrate has been in contact.

The two modes of the manufacturing methods of a micro electro mechanical system are each made to satisfy conditions for constituting the micro electro mechanical system. For example, the area of the opening portion is 0.01 mm$^2$ or more and 25 mm$^2$ or less. The total area of the opening portion provided in the first spacer layer is 20% or less of the whole area of the first spacer layer.

Then, one mode of a semiconductor device of the present invention is that a layer including an electric circuit, an electrode electrically connected to the electric circuit, a first spacer layer, a layer including a piezoelectric element, a second spacer layer and a second film substrate are formed over a substrate. Here, the layer including the piezoelectric element, the first spacer layer and the second spacer layer have the same structure as those of the above-described micro electro mechanical system.

Another mode of a semiconductor device of the present invention is that a layer including an electric circuit, an electrode electrically connected to the electric circuit, a first spacer layer, a functional layer including a particular functional element, a second spacer layer and a second film substrate are formed over a substrate. Here, the functional layer, the first spacer layer and the second spacer layer have the same structure as those of the above-described micro electro mechanical system.

In the two modes of the semiconductor device, the electric circuit includes a semiconductor element, and the electrode to be connected to the electric circuit is formed so as to connect the electric circuit with the piezoelectric element. In addition, the substrate constituting the semiconductor device is a film substrate, and a third spacer layer may be provided between the substrate and the layer including the electric circuit. Further, in the two modes, the second spacer layer can be formed with an anisotropic conductive adhesive agent.

One mode of a manufacturing method of a semiconductor device of the present invention is that a peeling layer, a layer including a piezoelectric element, and a first spacer layer are formed over a first substrate, and a first film substrate is attached thereonto. By utilizing that the layer including a piezoelectric element is attached to the first film substrate by the adhesiveness of the first spacer layer, the layer including a piezoelectric element is peeled from the substrate and transferred to the first film substrate. Then, a layer including an electric circuit, and an electrode electrically connected to the electric circuit are formed over a second substrate. Then, a second spacer layer is selectively formed either over the electrode formed over the layer including an electric circuit or the side of the layer including a piezoelectric element with which the substrate has been in contact, and the face on which an electrode for the layer including an electric circuit is formed is attached to the side on which the layer including a piezoelectric element has been in contact with the substrate.

In addition, another mode of a manufacturing method of a semiconductor device of the present invention is that a peeling layer, a functional layer including a particular functional element, and a first spacer layer are formed over a first substrate, and a first film substrate is attached thereonto. By utilizing the attachment of the functional layer to the first film substrate by the adhesiveness of the first spacer layer, the functional layer is peeled from the substrate and transferred to the first film substrate. Then, a layer including an electric circuit and an electrode electrically connected to the electric circuit are formed over a second substrate. Then, a second spacer layer is selectively formed either over the electrode formed over the layer including an electric circuit or the side of the functional layer with which the substrate has been in contact. Then, the face on which the electrode for the layer including an electric circuit is formed is attached to the side on which the functional layer has been in contact with the substrate.

Further, in the two modes of a manufacturing method of a semiconductor device, a peeling layer may be provided between the second substrate and the layer including an electric circuit, and the second substrate may be peeled from the layer including an electric circuit, so that the layer including an electric circuit is transferred to the first film substrate. Because the layer including an electric circuit is attached to the first film substrate, the layer including an electric circuit can be peeled off from the second substrate by giving a change to the peeling layer. After that, a second film substrate can also be attached to the peeled surface of the layer including an electric circuit through a third spacer layer having adhesiveness.

In accordance with the present invention in which an interspace is formed using spacer layers, processes of forming a sacrifice layer and etching the sacrifice layer are not required. As a result, there is no restriction on the etching time, and the yield can be improved. Further, an expensive etching apparatus is not required.

BRIEF DESCRIPTION OF DRAWINGS

In the accompanying drawings:

FIG. 8 is a block diagram showing a semiconductor device according to one aspect of the present invention;

DETAILED DESCRIPTION OF THE INVENTION

Embodiment Modes

Figure 1A:
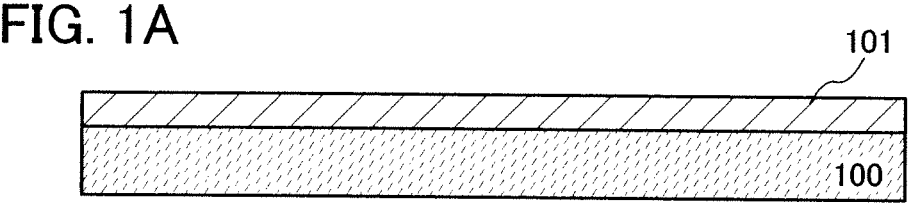
FIGS. 1A to 1C show a micro electro mechanical system according to one aspect of the present invention.

Hereinafter, the embodiment modes of the present invention will be described with reference to the accompanying drawings. It is easily understood by those skilled in the art that modes and details herein disclosed can be modified in various ways without departing from the spirit and the scope of the present invention. It should be noted that the present invention should not be interpreted as being limited to the description of the embodiment modes to be given below. Note that in all drawings showing the embodiment modes, the same reference numerals are used for the same portions or the portions having the same functions, and description thereof is omitted.

Embodiment Mode 1

Embodiment Mode 1 will describe a manufacturing process of a micro electro mechanical system in which an interspace is formed by using spacer layers.

A substrate 100 is prepared as shown in FIG. 1A. As the substrate 100, a substrate having an insulating surface (also referred to as an insulating substrate) such as a glass substrate, a quartz substrate, or a plastic substrate can be used. For example, when a plastic substrate is used, a highly flexible and lightweight micro electro mechanical system can be provided. In addition, a thin micro electro mechanical system can be provided by thinning a glass substrate by grinding and polishing, and so on. Further, a conductive substrate such as metal or a semiconductor substrate such as silicon can be used as the substrate 100. An insulating layer can be formed on a surface of such a substrate to be used.

A layer having an element which has a particular function (hereinafter, also referred to as a first functional layer) 101 is formed over the insulating substrate 100.

Figure 1B:
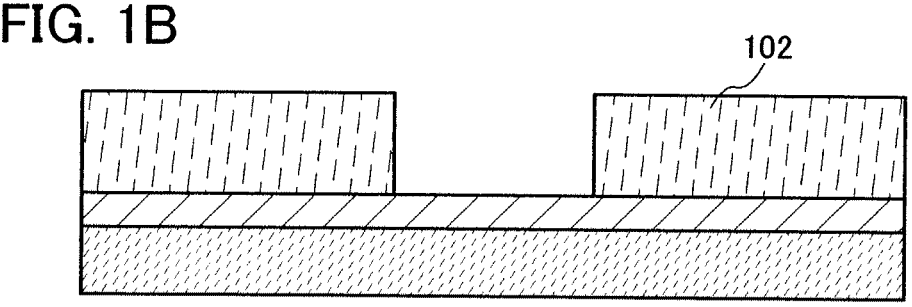

Then, as shown in FIG. 1B, a spacer layer 102 is selectively provided so as to form an opening portion over the first functional layer 101.

The spacer layer 102 preferably has an adhesive function. The spacer layer 102 attaches the functional layer 101 to a sealing substrate to be formed later, and an interspace is formed between the second functional layer 103 and the functional layer 101. An organic material or an inorganic material can be used as the spacer layer 102. As the organic material, compounds such as acrylic resin, polyimide resin, melamine resin, polyester resin, polycarbonate resin, phenol resin, epoxy resin, polyacetal, polyether, polyurethane, polyamide (nylon), furan resin, or diallyl phthalate resin can be used. In addition, many of such organic materials have an adhesive function. High-viscosity materials such as acrylic resin or polyimide resin can be formed by an application method, a spin coating method or a droplet-discharging method. The droplet-discharging method is a method in which a prepared composition is discharged from a nozzle in response to an electric signal to form a slight amount of a droplet and the droplet is attached on a desired position, and is also referred to as an inkjet method. As the inorganic material, silicon oxide, silicon nitride, and the like are given. The silicon oxide or silicon nitride can be formed by a CVD method or the like.

In order to selectively form the spacer layer like this, for example, a mask is formed in a region in which the spacer layer is not formed over the first functional layer 101. As the mask, a material can be used, which has no affinity with a material for forming the spacer layer, and repels the material for the spacer layer when the spacer layer is formed from above the mask, and by which the spacer layer is not formed in a portion in which the mask is formed. It is possible that the spacer layer is formed over the first functional layer 101, and the spacer layer is selectively formed by removing the mask. The manufacturing method like this is preferable when the spacer layer 102 is formed of an organic material. In addition, there is a method in which a spacer layer is formed entirely over the first functional layer 101, and a region in which the spacer layer is not formed is removed. In other words, a resist mask is formed by a photolithography method over the spacer layer formed over the first functional layer 101, and the spacer layer in a portion in which a resist mask is not formed, is removed by etching to selectively form the spacer layer 102. The manufacturing method like this can be applied when the spacer layer 102 is formed of an inorganic material. Additionally, by using a photosensitive cured resin material called a thick-film resist, the spacer layer is directly exposed to light and developed to be selectively formed.

Figure 1C:
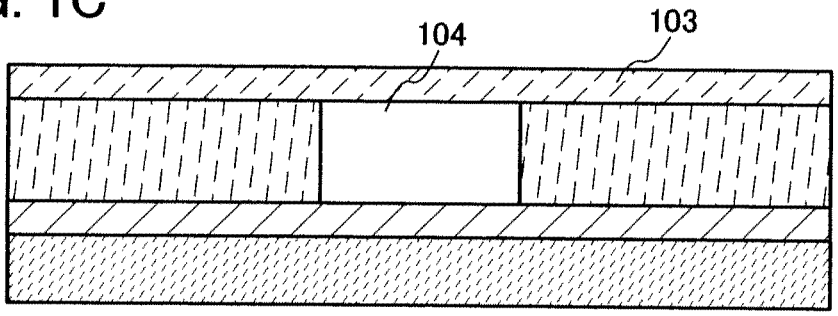

As shown in FIG. 1C, a second functional layer 103 is provided over the spacer layer 102. The second functional layer 103 can be selected from the same substrates which can be used for the insulating substrate. An interspace 104 is produced by providing the second functional layer 103 over the spacer layer 102. In other words, the interspace 104 is surrounded by the first functional layer 101 on its bottom side, the spacer layer 102 on its lateral side, and the second functional layer 103 on its top side.

A three-dimensional structure formed using the spacer layer 102 as stated above, is applied to various uses by making the first functional layer 101 and the second functional layer 103 function as follows:

(1) Each of the first functional layer 101 and the second functional layer 103 is made to function as an electrode, in particular, the first functional layer 101 is made to function as an electrode having sensitivity to an impulse caused by temperature, sound, voltage, or the like. In this manner, it may be possible to use the three-dimensional structure as a micro electro mechanical system, which senses the impulse caused by temperature, sound, voltage, or the like, such as a piezoelectric element, a thermoelectric element, or a strain resistor element.

(2) The first functional layer 101 and the second functional layer 103 are respectively made to function as an electric circuit and a layer including an element which deforms due to the impulse caused by temperature, sound, voltage, or the like (for example, a piezoelectric element, a thermoelectric element, and a strain resistor element are listed). In this case, the element which deforms due to the impulse caused by temperature, sound, voltage, or the like can deform easily because of the existence of the interspace 104. In this manner, it may be possible to use the three-dimensional structure as a semiconductor device including a micro electro mechanical system and an electric circuit.

It is to be noted that the interspace 104 is preferably filled with an inert gas such as nitrogen or a rare gas. This is because deterioration of the first functional layer 101 can be prevented.

Next, a case where the micro electro mechanical system manufactured as described above is peeled off from the substrate 100 will be described.

Figure 3A:
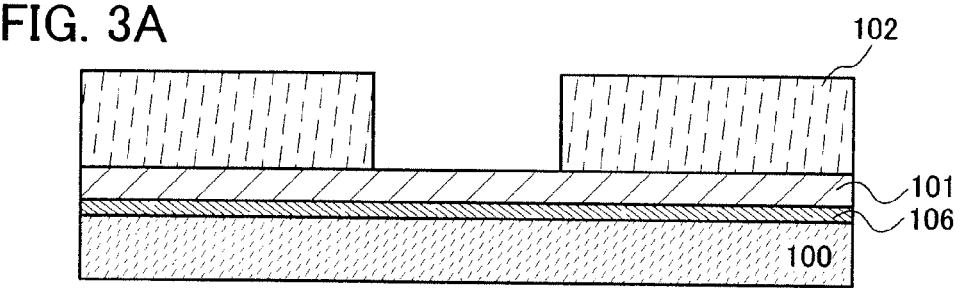
FIGS. 3A to 3D show a micro electro mechanical system according to one aspect of the present invention.

As shown in FIG. 3A, a peeling layer 106 is formed over the insulating substrate 100, and the first functional layer 101 and the spacer layer are formed. The peeling layer 106 is formed from a metal layer or a semiconductor layer. As the metal layer, a single layer or a stacked layer an element/elements selected from tungsten (W), titanium (Ti), tantalum (Ta), molybdenum (Mo), neodymium (Nd), nickel (Ni), cobalt (Co), zirconium (Zr), zinc (Zn), ruthenium (Ru), rhodium (Rh), palladium (Pd), osmium (Os), or iridium (Ir), or an alloy material or a compound material thereof can be used. The metal layer can be formed by a sputtering method using a metal as a target. The metal layer formed as the peeling layer has a thickness of 10 nm to 200 nm, preferably 50 nm to 75 nm. When a semiconductor layer is used as the peeling layer, it may include silicon. The structure may have any of an amorphous semiconductor, a semi-amorphous semiconductor (SAS) with a mixed state of an amorphous state and a crystal state, and a crystalline semiconductor. Such a semiconductor layer can be formed by a sputtering method, a CVD method, or the like. The semiconductor layer formed as the peeling layer may have a thickness of 30 nm to 1 μm, and 30 nm or less is also possible, as far as the thickness is within a thin film formation limit of a film formation apparatus.

Here, the number of opening portions may be one or more, and the area of one opening portion is 0.01 mm$^2$ or more and 25 mm$^2$ or less. The total area of the opening portions is preferably smaller than the total area of the spacer layer by 20 to 30%, in other words, it is preferably 70 to 80% of the total area of the spacer layer. This is made so that the peeling process can be conducted easily when also utilizing the adhesiveness of the spacer layer. For example, the area of the opening portion is larger than 70 to 80% of the spacer layer, the functional layer may be left on the surface of the substrate at the time of peeling. On the other hand, in order to secure the function of the interspace, the opening portion needs have a certain degree of size. Therefore, the area of the opening portions is set at 70 to 80% of the total area of the spacer layer.

Figure 3B:
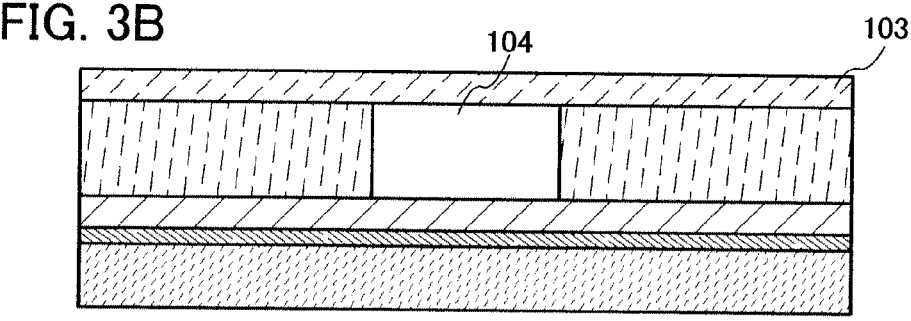

As shown in FIG. 3B, the second functional layer 103 is provided over the spacer layer 102. The material and the like of the second functional layer 103 are the same as those of the above-described embodiment mode, and the first functional layer 101 and the second functional layer 103 can be attached to each other, because the spacer layer 102 has an adhesive function. When the second functional layer 103 is provided over the spacer layer 102, the interspace 104 is generated, which is surrounded by the first functional layer 101 on its bottom side, the spacer layer 102 on its lateral side, and the second functional layer 103 on its top side.

Figure 3C:
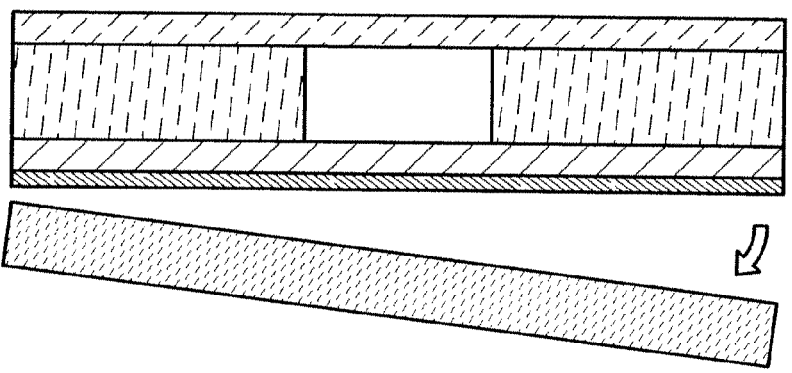

After that, as shown in FIG. 3C, the insulating substrate 100 is peeled off. At this time, the peeling can be done by utilizing the adhesiveness of the spacer layer 102 which is higher than the adhesiveness of the peeling layer 106. The adhesiveness of the peeling layer 106 can be reduced by giving a chemical or a physical change thereto. Then, the insulating substrate 100 can be peeled off. For example, when tungsten is used for the peeling layer 106, a heat treatment is conducted to generate a change in its crystal structure, thereby reducing the adhesiveness. As a result, the peeling occurs at an interface between the peeling layer 106 and the insulating substrate 100, at an interface between the peeling layer 106 and the first functional layer 101, or at the inside of the peeling layer 106, thereby peeling the insulating substrate 100 off from the first functional layer 101. In addition, when a semiconductor layer including silicon is used for the peeling layer 106, an opening portion which reaches the peeling layer 106 is provided and an etching agent is introduced to remove the peeling layer 106. As a result, the insulating substrate 100 is peeled off from the first functional layer 101. Gas or liquid can be used for the etching agent and an etching agent which selectively reacts only with the peeling layer is used. For example, as the etching gent which selectively reacts only with the semiconductor layer including silicon, halogen fluoride is given. As halogen fluoride, chlorine trifluoride (ClF$_3$) or hydrogen fluoride (HF) can be used.

Figure 3D:
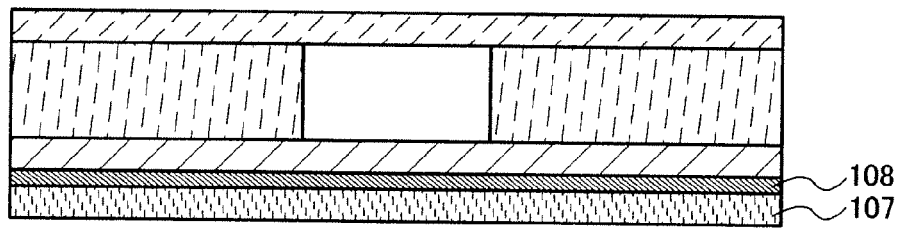

In this manner, the insulating substrate 100 can be removed. Further, the peeling layer 106 which is left on a rear side of the first functional layer 101 may be removed. Then, as shown in FIG. 3D, a film substrate 107 may be provided on the rear side of the first functional layer 101. When a film substrate is used also as the sealing substrate 103, a thin micro electro mechanical system having high flexibility can be provided. In addition, by providing a protective layer 108 on the rear side of the first functional layer 101, intrusion of impurity elements can be prevented. As the protective layer 108, silicon oxide or silicon nitride can be used. Moreover, the functional layer 101 and the film substrate 107 can be attached to each other by using an organic compound or the like.

As described above, one feature of the present invention is that the interspace is formed by using the spacer layer.

Embodiment Mode 2

Embodiment Mode 2 will describe another structure of a micro electro mechanical system in which an interspace is formed by a spacer layer.

Figure 2A:
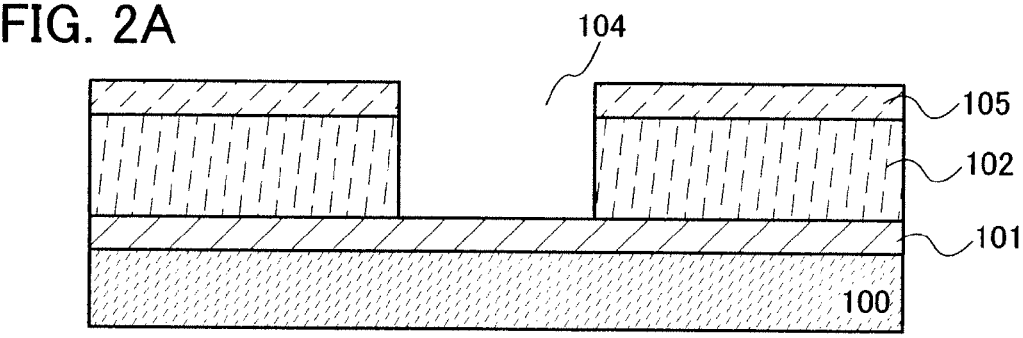
FIGS. 2A to 2C show a micro electro mechanical system according to one aspect of the present invention.

FIG. 2A shows a micro electro mechanical system having another structure, and is different from the micro electro mechanical system shown in FIG. 1C in that a sealing substrate 105 provided with an opening portion is formed. The other structures are the same as in FIG. 1C and thus, description thereof is omitted. The opening portion of the sealing substrate 105 has almost the same form as the opening portion provided in the spacer layer so as to be overlapped. In other words, the interspace 104 is surrounded by the first functional layer 101 on its bottom side, the spacer layer 102 and the sealing substrate 105 on its lateral side, and its top layer side is open. Like this, the form of the interspace is not necessarily closed.

Here, the explanations of the first functional layer 101 and the spacer layer 102 in the Embodiment Mode 1 are applied to the first functional layer 101 and the spacer layer 102 in this Embodiment Mode 2.

In addition, as in the above-described embodiment mode, the number of the opening portions may be one or more, and the area of one opening portion is 0.01 mm$^2$ or more and 25 mm$^2$ or less. The total area of the opening portions is preferably smaller than the area of the spacer layer by 20 to 30%. The spacer layer has a thickness of 10 μm or more, preferably 200 μm or less so as to secure the function of the opening portion. Moreover, this is done so that a peeling process to be described below is easily conducted.

Further, the opening portion is formed in accordance with an arrangement of the functional element included in the first functional layer 101. For example, in a semiconductor device where the first functional layer 101 and the second functional layer 103 respectively include a semiconductor element and a micro electro mechanical system, an opening portion is provided over an electrode connected to the semiconductor element, and a contact-type inspection of the semiconductor element included in the first functional layer 101 or an electric circuit formed from the semiconductor element can be conducted. In general, the inspection is conducted before providing the sealing substrate; however, according to the structure of the present invention, operation can be confirmed by contacting a probe with a wire or the like of the first functional layer 101 thorough the opening portion.

In the case of performing the contact-type inspection like this, the area of the opening portion is preferably 0.1×0.1 mm$^2$ to 1.0×1.0 mm$^2$ or more. The depth of the opening portion is equal to a sum of thicknesses of the spacer layer 102 and the second functional layer 103. Thus, when the depth of the opening portion is shallow, the thickness of the spacer layer 102 is small. When the opening portion is too deep, it is difficult to conduct the contact-type inspection; thus, it is preferable to control the thickness of the spacer layer.

Figure 2B:
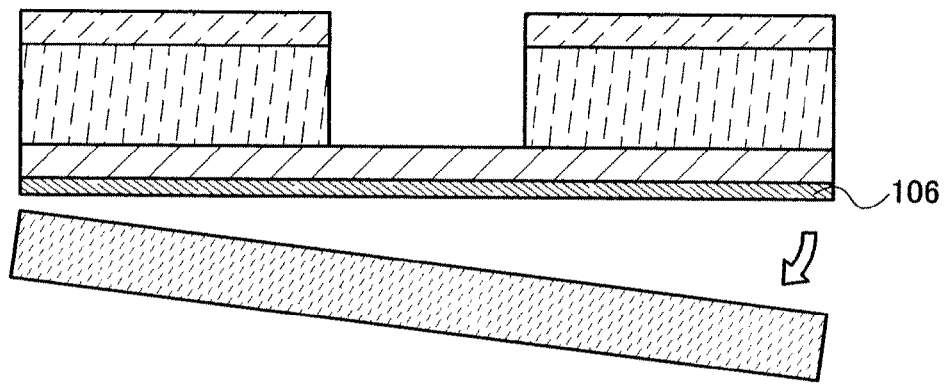

In addition, as in the above-described embodiment mode, the manufactured micro electro mechanical system can be peeled off from the substrate 100. As shown in FIG. 2B, in the micro electro mechanical system, the peeling layer 106, the functional layer 101 and the spacer layer are formed over the insulting substrate 100, and then the insulating substrate 100 is peeled off. The formation method and the peeling method of the peeling layer 106 can be the same as those of the above embodiment mode.

Figure 2C:
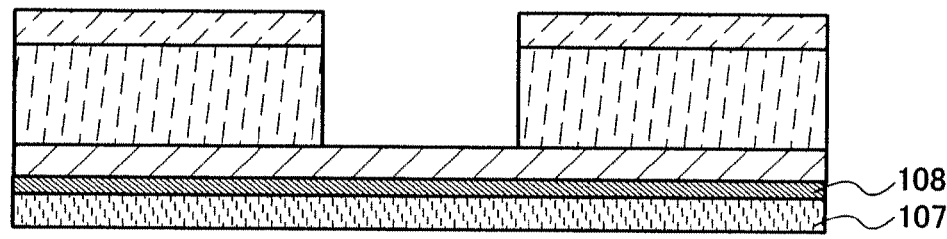

After that, as shown in FIG. 2C, the film substrate 107 may be provided on a rear side of the first functional layer 101. A protective layer 108 is provided between the first functional layer 101 and the film substrate 107. The film substrate 107 and the protective layer 108 can be provided in the same manner as in the above embodiment mode. In addition, the protective layer 108 can be attached to the first functional layer 101 after being formed over the film substrate 107. In this case, the protective layer 108 serves as an adhesive layer for adhering the film substrate to the first functional layer 101.

By providing an opening portion in the second functional layer 105 in this manner, a contact type inspection of the first functional layer 101 can be conducted even after transferring the first functional layer 101 to the film substrate 107. For example, when the first functional layer 101 is peeled off as described above, and transferred to the film substrate 107, characteristics of the element included in the functional layer are changed in some cases. In such a case, measurement of an element or an electric circuit can be conducted before the peeling and/or after transferring, as described in this embodiment mode. In this manner, measurement is conducted in each process, and thus the process can be controlled.

As described above, one feature of the present invention is that the interspace is formed by the spacer layer and the opening portion is also formed in the sealing substrate.

Embodiment Mode 3

Embodiment Mode 3 will describe a manufacturing method of a micro electro mechanical system having an interspace as described above, and a semiconductor device having an electric circuit formed from a semiconductor element.

Figure 4A:
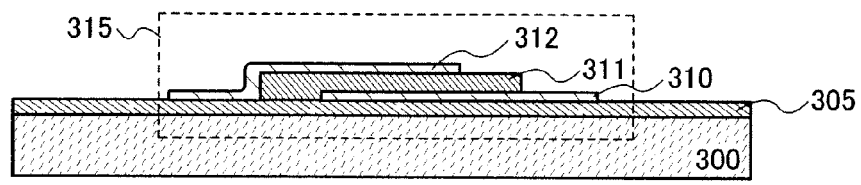
FIGS. 4A to 4D show a substrate for a piezoelectric element according to one aspect of the present invention.

As shown in FIG. 4A, a peeling layer 305 is formed over an insulating substrate 300. The insulating substrate 300 and the peeling layer 305 can be manufactured in the same manner as in the above-described embodiment mode. A layer including a piezoelectric element 315 is provided over the peeling layer 305 as the functional layer in the above-described embodiment mode. The piezoelectric element 315 has a structure in which a piezoelectric material 311 is formed over a first electrode 310, and a second electrode 312 is formed over the piezoelectric material (for example, ceramic material) 311. A film made of an element selected from aluminum (Al), titanium (Ti), molybdenum (Mo), tungsten (W) or silicon (Si), or an alloy film using some of the elements described above can be used for the first electrode 310 and the second electrode 312. As the piezoelectric material (ceramic material) 311 which becomes a piezoelectric layer (for example, ceramic layer), for example, quartz ($SiO_2$), barium titanate ($BaTiO$), lead titanate ($PbTiO_3$), lead zirconate titanate ($Pb(Zr,Ti)O_3$), lead lanthanum zirconate titanate ($(Pb,La)(Zr,Ti)O_3$), lithium niobate ($LiNbO_3$), lead metaniobate ($PbNb_2O_6$), polyvinylidene fluoride (PVDF), zinc oxide (ZnO), nitride aluminum (AlN), or tantalum oxide ($Ta_2O_5$) can be used for example. The piezoelectric material is an insulator which has no crystal center. When the piezoelectric material is applied with power to be strained and the crystal is polarized, charges are generated in the surface. This is called a piezoelectric effect. On the other hand, when the piezoelectric material is applied with voltage, a strain is generated. This is called an inverse piezoelectric effect. Accordingly, the piezoelectric material is oscillated, when it is applied with an alternating voltage.

Here, the case in which the layer including the piezoelectric element 315 is provided is shown as an example; however, a layer including a particular functional element which can be formed by stacking thin films can be formed. Here, as the particular functional element, various functional elements can be used, such as a passive element and a negative element, for example, a thermoelectric element, a strain resistor element, an inductor and a capacitor, in addition to a piezoelectric element.

Figure 4B:
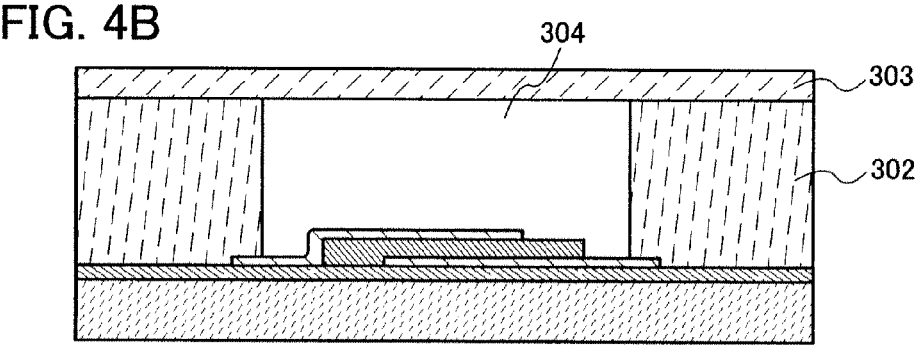

After that, as shown in FIG. 4B, a spacer layer 302 is selectively formed over or on the side of the piezoelectric element. As shown in FIG. 4B, a portion in which the piezoelectric element is formed becomes a non-formation region of the spacer layer 302, i.e., an opening portion. Here, the piezoelectric element is formed by stacking the first electrode 310, the piezoelectric material 311 and the second electrode 312. By providing the sealing substrate 303 over the spacer layer 302, an interspace 304 is generated. In other words, the interspace 304 is surrounded by the piezoelectric element 315 on its bottom side, the spacer layer 302 on its lateral side, and the sealing substrate 303 on its top side. When the piezoelectric element 315 like this is deformed by surrounding pressure, the voltage between the first electrode 310 and the second electrode 312 is changed. By reading the change of the voltage, the pressure can be measured.

The micro electro mechanical system having the piezoelectric element like this can be applied to sensors (typically, pressure sensors), actuators, oscillation circuits and filters.

Figure 4C:
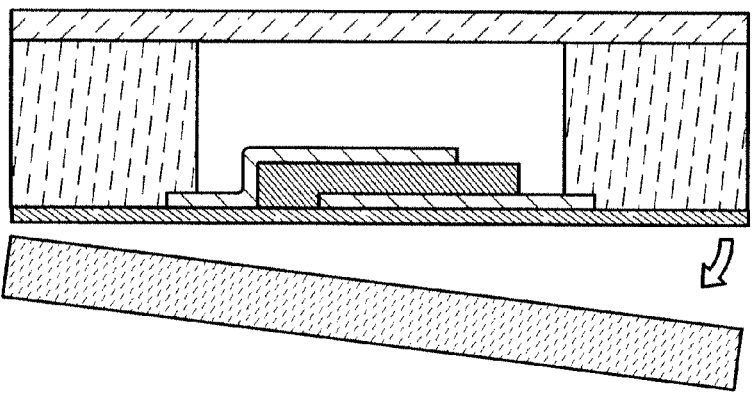

As shown in FIG. 4C, the substrate 300 is peeled off. The peeling method of the insulating substrate 300 is the same as the peeling method of the insulating substrate 100 described in the above embodiment mode.

Figure 4D:
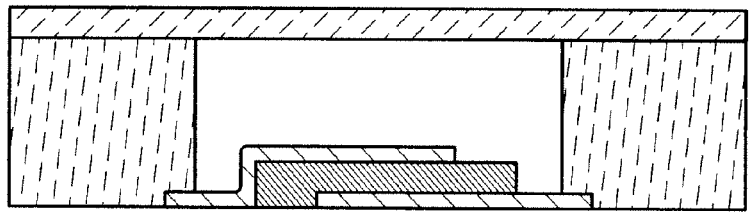

As shown in FIG. 4D, the peeling layer 305 may be removed. Then, a film substrate or a protective film may be formed on a rear side of the piezoelectric element 315.

As described above, the piezoelectric element which is adjacent to the interspace formed using the spacer layer can be formed.

Figure 5:
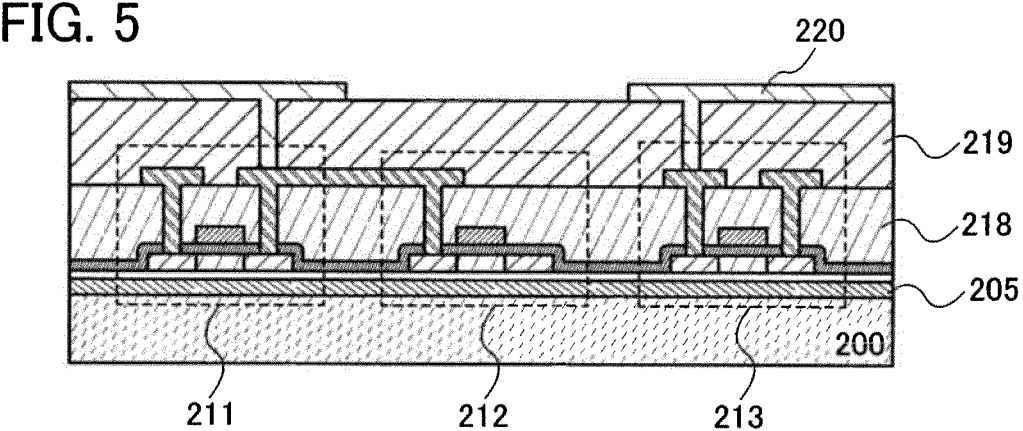
FIG. 5 shows a TFT substrate according to one aspect of the present invention.

Next, a method for forming an electric circuit which is connected to the piezoelectric element will be described with reference to FIG. 5. Here, the electric circuit includes a control circuit or the like which controls the piezoelectric element 315 or receives an output signal from the piezoelectric circuit 315. The control circuit or the like is formed with thin film transistors or the like. Note that in this specification, a substrate provided with a thin film transistor (TFT) is referred to as a TFT substrate.

A thin film transistor includes a semiconductor film, a gate electrode, a gate insulating film, a source electrode and a drain electrode, and can be formed by a known method. The semiconductor film may be amorphous, microcrystalline or crystalline. When a highly crystalline semiconductor film is used, electric characteristics of the thin film transistor can be enhanced and can be preferably used for an electric circuit. In this embodiment mode, thin film transistors 211, 212 and 213 are provided over the insulating substrate 200. Note that the thin film transistors 211, 212 and 213 are preferably provided over the insulating substrate 200 with a peeling layer 205 therebetween so as to peel the insulating substrate 200 off later. An insulating layer 218 is preferably formed to planarize the surfaces of the thin film transistors. The insulating layer 218 is formed over the thin film transistors 211, 212 and 213 and opening portions are provided in the insulating layer 218 to form source electrodes and drain electrodes. The source electrodes and the drain electrodes serve also as source wires and drain wires respectively. An insulating layer 219 is formed over the source electrode and the drain electrode, and a connection terminal 220 connected to the source electrode, the drain electrode or the gate electrode is formed over the insulating layer 219. In this embodiment mode, a mode in which the source wire or the drain wire is connected to the connection terminal 220 is shown; however, a gate wire may be connected. For example, when the connection terminal 220 is connected to the gate wire, given that the voltage of the connection terminal 220 is equal to or higher than a desired voltage, the thin film transistor connected to the gate wire is turned ON. Here, the insulating layer 218 and the insulating layer 219 are formed so as to insulate each thin film transistor, wires over and under the thin film transistors, and wires which are adjacent to each other. The insulating layers are formed so as to planarize the top surface of the functional layer provided with a thin film transistor or a wire. The insulating layers 218 and 219 can be formed from an inorganic material or an organic material. When an organic material is used for the insulating layers, the planarity thereof can be easily enhanced. The connection terminal 220 is preferably provided as a pad having a large area so as to make easy connection with the piezoelectric element possible. In this manner, a control circuit including a thin film transistor can be formed.

Naturally, the control circuit can be formed with MOSFET manufactured on a silicon wafer. However, a thin film transistor formed over the insulating substrate can be used to reduce the manufacturing cost.

Figure 6A:
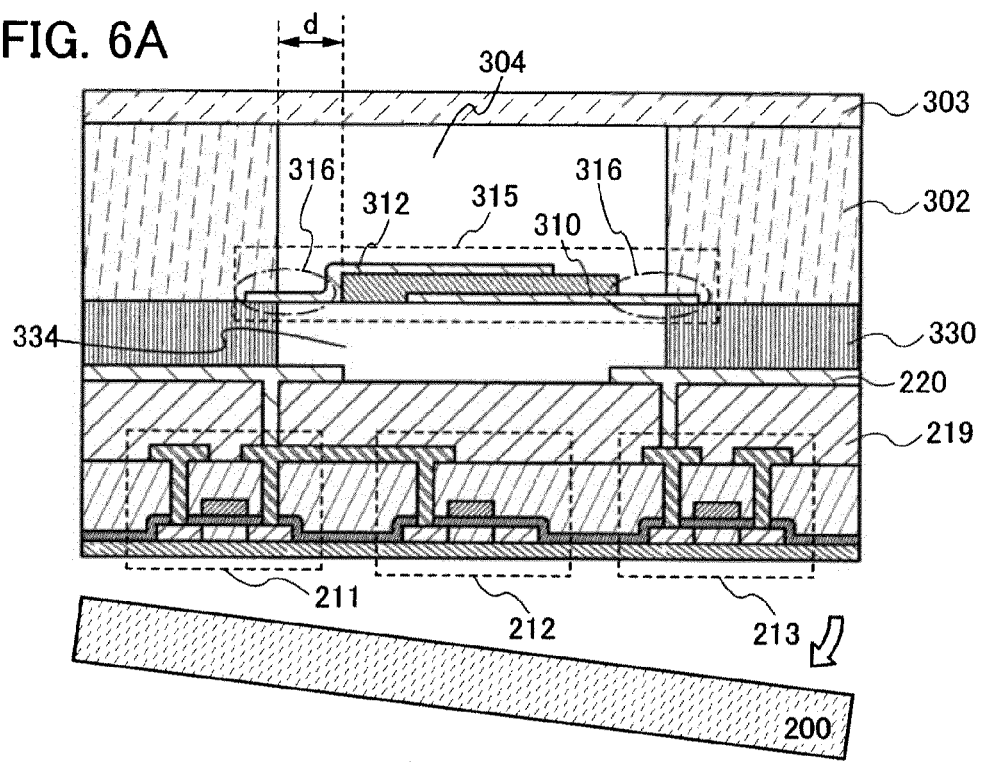
FIGS. 6A and 6B show a micro electro mechanical system according to one aspect of the present invention.

Then, a piezoelectric element is attached to the TFT substrate so as to connect the control circuit with the piezoelectric element. For example, as shown in FIG. 6A, the connection terminal 220 is connected to the first electrode 310 and the second electrode 312 of the piezoelectric element in a connection region 316. When the piezoelectric element 315 is formed, the peeling layer 305 is removed, thereby exposing the first electrode 310 and the second electrode 312. As the connection method, an anisotropic conductive agent (or anisotropic conductive film: ACF) 330 can be used. The ACF can have conduction only in one direction, and thus, connection between the connection terminal 220 and the first electrode 310 and between the connection terminal 220 and the second electrode 312 can be made. The distance d between the anisotropic conductive agent 330 and the piezoelectric material forming a piezoelectric element, i.e., the distance d from an end of the piezoelectric material to an end of the opening portion is preferably 10 μm or more and 100 μM or less. An area of the interspace formed by the anisotropic conductive agent 330 is preferably larger than the area of a portion in which the piezoelectric material is provided.

The anisotropic conductive agent 330 serves also as a spacer layer. In addition, the anisotropic conductive agent is preferably formed in a region which is considered to be the same as the spacer layer 302 (or almost the same region). Further, it preferably has the form which can be considered to be the same as the spacer layer 302 (or almost the same form). Thus, the interspace formed by the spacer layer 302 can be disposed to be overlapped with the interspace formed by the anisotropic conductive agent 330.

An interspace 334 is generated by selectively forming the ACF 330. The interspace 334 is surrounded by the insulating layer 219 and the connection terminal 220 on its bottom side, the ACF 330 on its lateral side, and the piezoelectric element 315 on its top side. Accuracy can be enhanced by providing the interspaces 304 and 334 over and under the piezoelectric element 315. However, when the ACF 330 is provided entirely without forming the interspace 334, the micro electro mechanical system can be used as a pressure sensor.

After that, the insulating substrate 200 is peeled off. The peeling of the insulating substrate 200 is the same as the peeling method of the insulating substrate 100 of the above embodiment mode. The semiconductor device shown in FIG. 6A is manufactured as stated above.

Figure 6B:
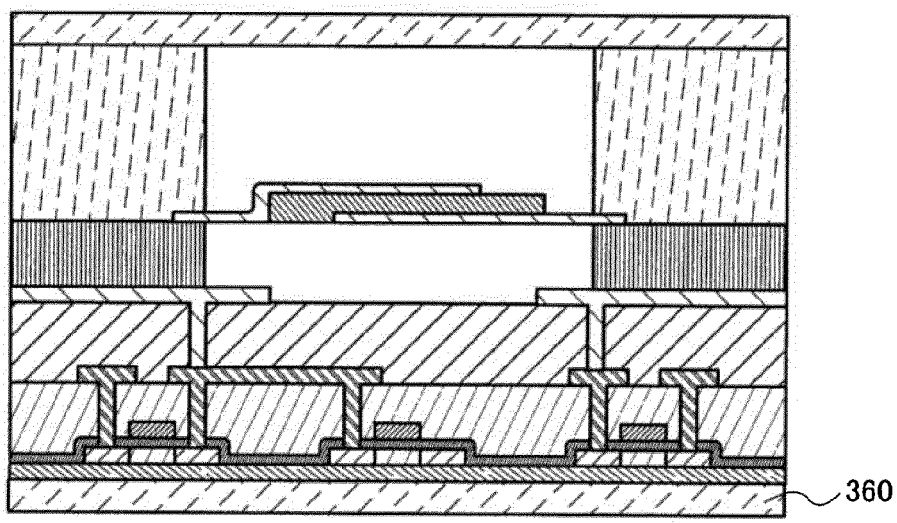

As shown in FIG. 6B, a film substrate 360 is provided below the thin film transistors 211, 212 and 213. At this time, the film substrate 360 may be provided after removing the peeling layer 205. If a film substrate is used also for the sealing substrate 303, a semiconductor device having thinness and highly flexibility can be provided.

Figure 7A:
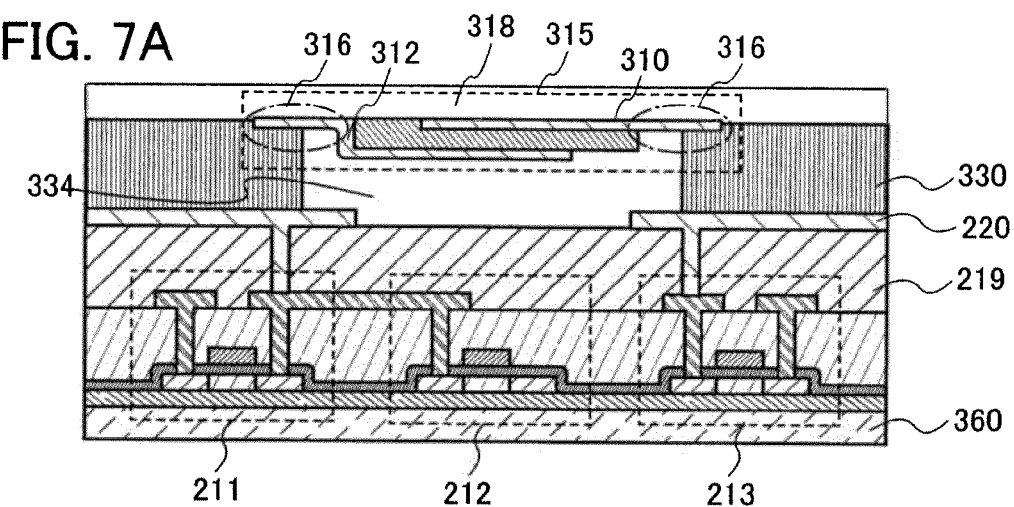
FIGS. 7A and 7B show a micro electro mechanical system according to one aspect of the present invention.

In addition, in FIG. 7A, a semiconductor device having a micro electro mechanical system in which the piezoelectric element 315 is inverted and attached to the TFT substrate, and the connection terminal 220 is electrically connected to the connection region 316, is shown. The piezoelectric element is attached to the TFT substrate in a state that the insulating substrate 300 for the piezoelectric element 315 is peeled; however, it may be attached to the TFT substrate in a state that the insulating substrate 300 is not peeled. An interspace 334 is generated by inverting the piezoelectric element 315 and attaching it to the TFT substrate. The interspace 334 is surrounded by the insulating layer 219 and a part of the connection terminal 220 on its bottom side, the ACF 330 on its lateral side, and the piezoelectric element 315 on its top side. The other structures are the same as those in FIGS. 6A and 6B, and thus description is omitted. It is to be noted that it is preferable to provide a protective film 318 in contact with the piezoelectric element 315 in order to prevent piezoelectric element 315 from being damaged. The protective film 318 is preferably formed from a resin material such as polyimide, or epoxy resin; however, an inorganic material such as silicon oxide, or silicon nitride may be used to form the protective film 315 as long as the protective film 315 has a thickness thin enough not to prevent the operation of the piezoelectric element 315.

In this manner, by inverting the piezoelectric element and attaching it, there is no need that a wire of the connection region 316 is deliberately exposed. In other words, because the piezoelectric element is inverted and attached, the piezoelectric element can be attached to the TFT substrate without peeling the insulating substrate 300 and can be electrically connected to the connection terminal 220. Therefore, the number of steps can be expected to be reduced, as a result of inverting the piezoelectric element and attaching it to the TFT substrate.

Figure 7B:
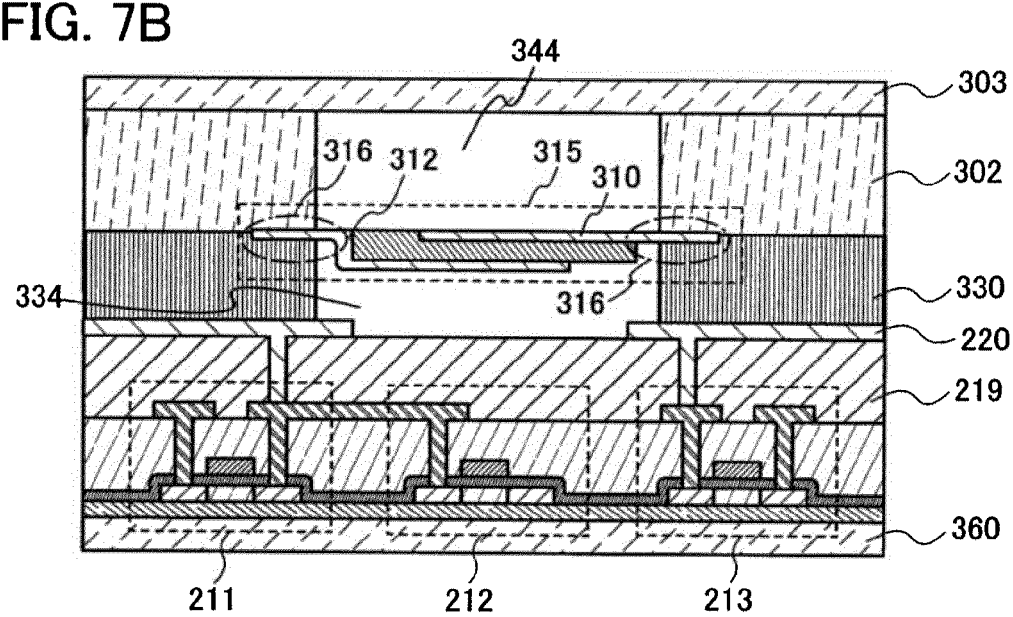

FIG. 7B shows a case in which the substrate 303 is provided through the spacer layer 302 in the structure of FIG. 7A. An interspace 344 is generated by providing the substrate 303 through the spacer layer 302. The interspace 334 is surrounded by the piezoelectric element 315 on its bottom side, the spacer layer 302 on its lateral side, and the substrate 303 on its top side. It is to be noted that the substrate 303 is preferably formed from a resin such as polyimide, or epoxy resin to have flexibility. The other structures are the same as those of FIG. 7A, and description thereof is omitted. The interspace 334, and 344 is filled with a rare gas or an inert gas such as nitrogen gas. The semiconductor device having a structure like this can be operated as follows. Firstly, it is to be noted that pressure of outside of the semiconductor, pressure in the interspace 334, and pressure in the interspace 344 are respectively referred to as P1, P2, and P3 (in the initial state, values of P3 and P2 are equal). When a pressure difference between P1 and P2 changes due to variation of P1, the substrate will deform, and capacity V1 of the interspace 334 will change. The change of capacity V1 will cause change of P2. As a result, a pressure difference between P2 and P3 will cause deformation of the piezoelectric element 315. The signal caused by the deformation of the piezoelectric element 315 will be detected by the electric circuit having TFT 212.

The micro electro mechanical system having a plurality of interspaces like this is expected to be used for applications utilizing a volume difference of the interspaces. For example, when a micro electro mechanical system is applied to a pressure sensor, a first interspace having a large volume, i.e., a large surface area, is used as a detection surface, and a second interspace having a smaller volume than the first interspace is used for detecting a pressure change, thereby increasing detection sensitivity. In addition, the number of the interspaces is not limited to two, and more than two interspaces may be provided.

Embodiment Mode 4

Figure 13A:
FIGS. 13A to 13C show a filter according to one aspect of the present invention.

Embodiment Mode 4 will describe a mode in which a micro electro mechanical system is applied to a filter. As shown in FIG. 13A, a filter has a rectification function in which a particular frequency band from a composite wave in which a plurality of frequencies are overlapped, is allowed to pass through the filter or is blocked. In other words, a composite wave which passes the filter can be obtained as a rectified wave. The filter can be used for electronic devices which conduct wireless communication, such as portable phones, PDAs (personal digital assistants), or cards including wireless chips.

Figure 13B:
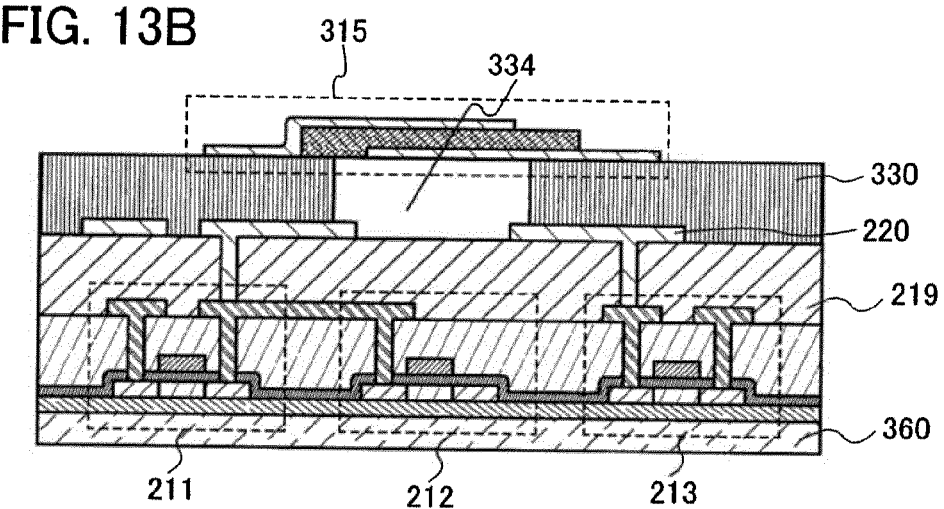

FIG. 13B shows a structural example of a micro electro mechanical system which can be applied to a filter. As in the above-described embodiment modes, the ACF 330 is selectively formed over the TFT substrate provided with the TFTs 211, 212 and 213, and the piezoelectric element 315 is attached so that the connection terminal 220 and a connection region of the piezoelectric element 315 are electrically connected. Thus, the interspace 334 is generated. The interspace 334 is surrounded by the insulating layer 219 and a part of the connection terminal 220 on its bottom side, the ACF 330 on its lateral side, and the piezoelectric element 315 on its top side. The piezoelectric element forming the filter may be circular, oval or polygon. Further, a plurality of piezoelectric elements can be connected in parallel or in serial to form a filter. In the case where it is used as a filter, the surface of the piezoelectric element 315 may be exposed. A protective film made of an insulator may be provided over the piezoelectric element 315 so as to secure the strength.

Figure 13C:
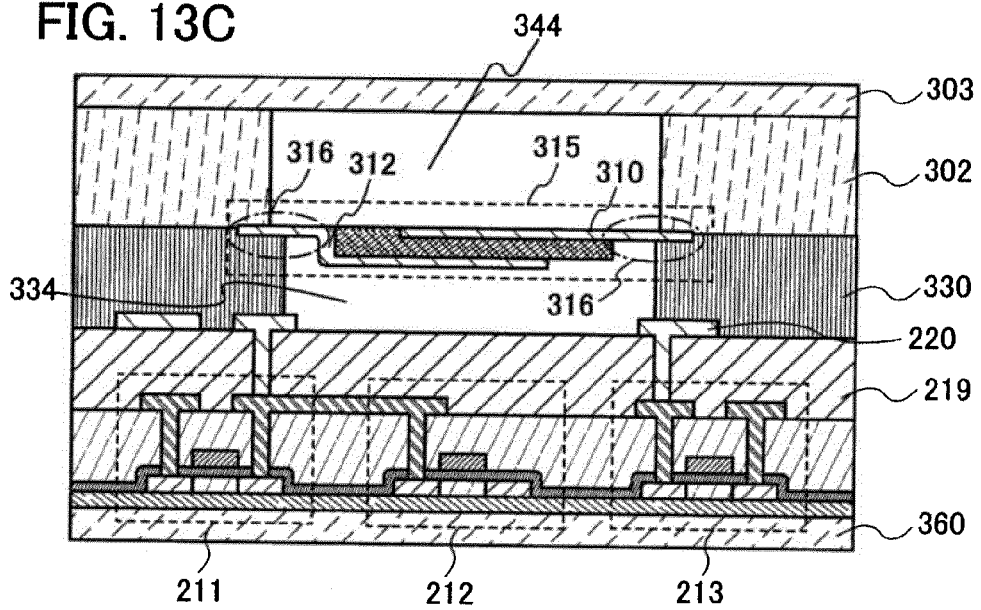

FIG. 13C shows a different structure from FIG. 13B in that the piezoelectric element 315 is inverted and attached to the TFT substrate, and a plurality of interspaces are provided over and under the piezoelectric element. The other structures are the same as in the above embodiment modes, and thus, description is omitted. Naturally, a plurality of interspaces can be provided, without inverting the piezoelectric element 315 as in FIG. 13B. The interspace 344 provided over the piezoelectric element 315 is generated by attaching the substrate 303 through the spacer layer 302. In other words, the interspace 344 is surrounded by the piezoelectric element 315 on its bottom side, the spacer layer 302 on its lateral side, and the sealing substrate 303 on its top side. The interspace 344 may be formed to have the same volume as the interspace 334. By making the volumes of the interspace 334 and the interspace 344 equal, their inner pressures can be made equal easily. The forms of the interspaces 334 and 344 may be rectangular, circular, polygon or oval.

By forming a filter using a micro electro mechanical system of the present invention in this manner, processes of forming a sacrifice layer of a micro crystal structure body and etching the sacrifice layer are not needed. As a result, there is no restriction on the etching time, and the yield can be improved. Further, an expensive etching apparatus is not required.

Embodiment Mode 5

Figure 14A:
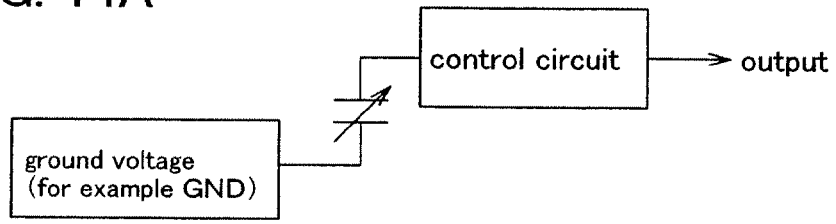
FIGS. 14A to 14C show a pressure sensor according to one aspect of the present invention.

Embodiment Mode 5 will describe a mode in which a micro electro mechanical system is applied to a sensor. As shown in FIG. 14A, a pressure sensor utilizes a phenomenon that one electrode of a piezoelectric element is connected to a constant voltage (for example, a ground voltage (GND)), and a voltage of the other electrode is changed by the inverse piezoelectric effect of the piezoelectric element which is deformed by being applied with pressure. The pressure sensor input this voltage change into a control circuit, and has a function of amplifying or processing the voltage change and outputting it. A pressure sensor like this can be mounted as a part of a feedback mechanism in controlling pressure fluctuation or the like inside a film formation apparatus for example, in the case of controlling pressure fluctuation.

Figure 14B:
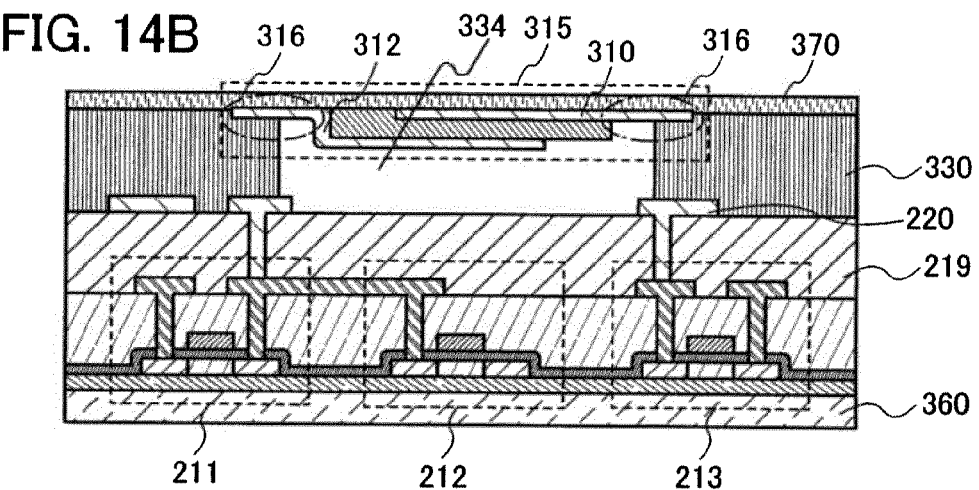

FIG. 14B shows a structural example of a micro electro mechanical system which can be applied to a pressure-sensor. As in the above-described embodiment mode, an ACF 330 is selectively formed in the TFT substrate provided with the thin film transistors (TFTs) 211, 212 and 213 etc., and the piezoelectric element 315 is inverted and attached so as to electrically connect the connection terminal 220 and the connection region of the piezoelectric element 315. Thus, an interspace 334 is generated. The interspace 334 is surrounded by the insulating layer 219 and a part of the connection terminal 220 on its bottom side, the ACF 330 on its lateral side, and the piezoelectric element 315 on its top side.

When it is used as a pressure sensor, it is preferable that the piezoelectric element 315 is not exposed. This is for maintaining sensitivity of pressure. Thus, in this embodiment mode, the piezoelectric element 315 is inverted to form the interspace 334 and a rear side of the piezoelectric element 315 is covered by a protective film made of an insulator. The protective film is preferably formed using a material which easily conducts pressure, more preferably, which is easily deformed elastically but difficulty in deforming plastically. In the pressure sensor like this, the volume of the interspace 334 is changed, i.e., external pressure can be measured by the change of pressure.

Figure 14C:
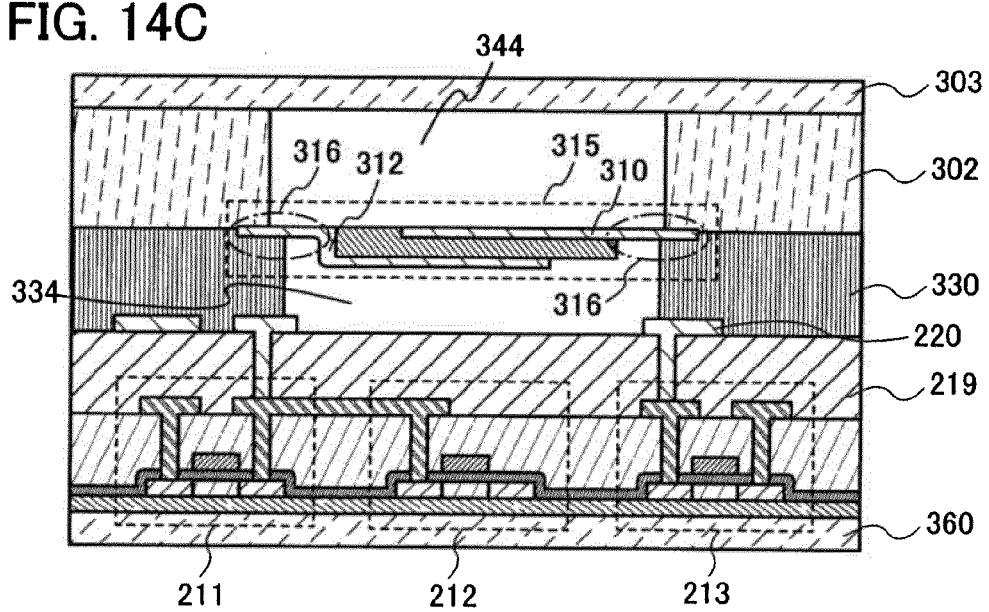

FIG. 14C shows a pressure sensor having a different structure in that a plurality of interspaces are provided over and under the piezoelectric element. The other structures are the same, and thus description is omitted. A detection face of pressure is preferably a face opposite to the TFT substrate, and thus, in the case of using a micro electro mechanical system as a pressure sensor, the piezoelectric element may be inverted and attached to the TFT substrate. The interspace 344 provided over the piezoelectric element 315 is generated by attaching the sealing substrate 303 through the spacer layer 302. In other words, the interspace 344 is surrounded by the piezoelectric element 315 on its bottom side, the spacer layer 302 on its lateral side, and the sealing substrate 303 on its top side. The interspace 344 may be formed to have the same inner pressure as the interspace 334. By providing the plurality of interspaces and making inner pressure of each interspace different, sensitivity of detection can be increased. For example, a first interspace having a large volume, i.e., a large surface area is used as a detection surface, even if a second interspace has a smaller volume, the detection surface of the second interspace is large, thereby increasing detection sensitivity.

By forming a pressure sensor using a micro electro mechanical system of the present invention, processes of forming a sacrifice layer of a micro crystal structure body and etching the sacrifice layer are not needed. As a result, there is no restriction on the etching time, and the yield can be improved. Further, an expensive etching apparatus is not required. Moreover, by applying the piezoelectric element of the present invention, electrical power saving and simplification of a structure can be tried to be achieved.

Embodiment Mode 6

Embodiment Mode 6 will describe a semiconductor device which has a micro electro mechanical system and which is capable of conducting wireless communication.

FIG. 8 shows a detailed structure of an electric circuit 604 of a semiconductor device 601. The electric circuit 604 has functions of receiving an electromagnetic wave emitted from outside (here, reader/writer 607) to generate electric power for driving the semiconductor device 601, and carrying out wireless communication with outside. Therefore, the electric circuit 604 has a power source circuit 611, a clock generating circuit 612, a modulating circuit 613, a demodulating circuit 614, a decoding circuit 616, an encoding circuit 617, an information judging circuit 618, and the like, which are necessary for wireless communication. Moreover, in some cases, the electric circuit has a different structure depending on frequency or a communication method of an electromagnetic wave used for the wireless communication.

Moreover, the electric circuit 604 has functions of controlling the micro electro mechanical system 603, processing information from the reader/writer 607, and so on. Therefore, the electric circuit 604 has a memory, a memory controlling circuit, an arithmetic circuit, and the like. FIG. 8 shows a structure in which the electric circuit 604 has a memory 621, a memory controlling circuit 622, an arithmetic circuit 623, a microstructure controlling circuit 624, an A/D converting circuit 625, and a signal amplifying circuit 626.

The power source circuit 611 has a diode and a capacitor, and can hold constant voltage by rectifying alternating voltage generated at the antenna 602 and supply the constant voltage to each circuit. The clock generating circuit 612 has a filter or a frequency dividing circuit, by which a clock with required frequency can be generated based on alternating voltage generated at the antenna 602 and the clock can be supplied to each circuit.

An element including one or more piezoelectric elements manufactured in accordance with the above-described embodiment modes can be applied to the filter. The filter manufactured according to a manufacturing method of the present invention can be formed to be integrated over the same substrate as other circuits. As a result, a troublesome step of packaging or occurrence of detective connections can be reduced. Here, a frequency of a clock generated by the clock generating circuit 612 is basically equal to or lower than a frequency of the electromagnetic wave used for communication between the reader/writer 607 and the semiconductor device 601. In addition, the clock generating circuit 612 includes a ring oscillator and can produce a clock having an arbitrary frequency by voltage input from the power source circuit 611.

The demodulating circuit 613 has a filter and an amplifying circuit, so that a signal included in alternating voltage generated at the antenna 602 can be demodulated. The demodulating circuit 613 has a circuit having a different structure depending on a modulation method used for the wireless communication. The decoding circuit 615 decodes a signal which has been demodulated by the demodulating circuit 113. This decoded signal is a signal which has been sent from the reader/writer 607 or not. The information judging circuit 617 has a comparing circuit and the like, and can judge whether the decoded signal is a correct signal that has been sent from the reader/wrier 607. If the signal is judged to be correct information, the information judging circuit 617 can send a signal showing that the signal is correct to each circuit (such as the memory controlling circuit 622, the arithmetic circuit 623, or the microstructure controlling circuit 624), and the circuit having received the signal can carry out predetermined operation.

The encoding circuit 616 encodes data to be sent from the semiconductor device 601 to the reader/writer 607. The modulating circuit 614 modulates the encoded data and sends the modulated data to the reader/writer 607 through the antenna 602.

The data to be sent to the reader/writer is data specific to the semiconductor device stored in a memory or data obtained by a function of the semiconductor device. The data specific to the semiconductor device is data such as identification information, which is memorized in a nonvolatile memory of the semiconductor device, for example. The data obtained by a function of the semiconductor device is, for example, data obtained by the micro electro mechanical system, data to which certain calculation has been conducted based on the data obtained by the micro electro mechanical system, and the like.

The memory 621 can have a volatile memory and a nonvolatile memory, and store data specific to the semiconductor device 601 (identification information), information obtained from the micro electro mechanical system 603, and the like. Although FIG. 8 shows only one memory 621, it is possible to have a plurality of types of memories in accordance with the kind of information to be stored and a function of the semiconductor device 601. The memory controlling circuit 622 controls the memory 621 in the case of reading information stored in the memory 621 and writing information in the memory 621. Specifically, the memory controlling circuit 622 can generate a writing signal, a reading signal, a memory selecting signal, and the like, and specify an address, and so on.

The microstructure controlling circuit 624 can generate a signal for controlling the micro electro mechanical system 603. For example, in the case of controlling the microstructure 13 in accordance with an instruction from the reader/writer 607, a signal for controlling the micro electro mechanical system 603 is generated based on the signal decoded by the decoding circuit 615. In the case where data such as a program for controlling operation of the micro electro mechanical system 603 is stored in the memory 621, a signal for controlling the micro electro mechanical system 603 is generated based on the data read from the memory 621. Besides, it can have a feedback function for generating a signal for controlling the micro electro mechanical system 603 based on data in the memory 621, data from the reader/writer 607, and data obtained from the micro electro mechanical system 603.

The arithmetic circuit 623 can process data obtained from the micro electro mechanical system 603, for example. Moreover, the arithmetic circuit 623 can carry out information processing and the like in the case where the microstructure controlling circuit 624 has a feedback function. The A/D converting circuit 625 is a circuit for converting analog data and digital data and transmits a control signal to the micro electro mechanical system 603. Alternatively, the A/D converting circuit 625 can convert data from the micro electro mechanical system 603 and transmit the data to each circuit. The signal amplifying circuit 626 can amplify a weak signal obtained from the micro electro mechanical system 603 and transmits the amplified signal to the A/D converting circuit 625.

By using the semiconductor device like this, wireless communication can be conducted.

Embodiment Mode 7

Embodiment Mode 7 will describe an appearance of a semiconductor device.

Figure 9A:
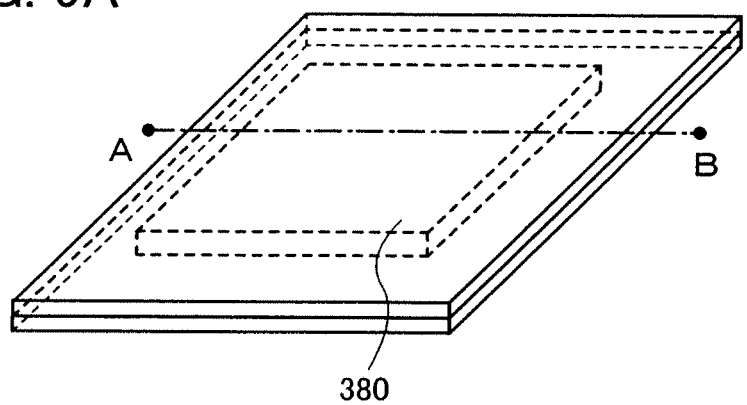
FIGS. 9A and 9B show an appearance of a semiconductor device according to one aspect of the present invention.

FIG. 9A is a perspective view showing an appearance of a semiconductor device. A semiconductor device 380 is packed by sealing substrates 303 and 360 made of film materials.

Figure 9B:
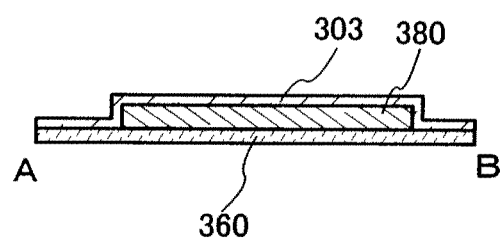

FIG. 9B shows a cross section taken along A-B of FIG. 9A. Here, FIG. 9A shows a simplified view of the cross section of the semiconductor device shown in FIGS. 6A and 6B. As in the above-described embodiment modes, the semiconductor device 380 is covered with the sealing substrates 303 and 360.

As described in the above embodiment modes, the interspace included in the semiconductor device is controlled to have a reference pressure. In the case of measuring a pressure around the atmospheric pressure, the interspace is in the atmospheric pressure or a pressure around the atmospheric pressure. For example, when it has a pressure lower than the atmospheric pressure, the electrodes of the piezoelectric element bend the interspace side (inward). Then, when the semiconductor device is arranged in the interspace having a predetermined pressure, the electrode state of the piezoelectric element is changed in accordance with the pressure of the interspace. The pressure of the interspace can be measured from the electrode state of the piezoelectric element. Thus, when a pressure of high vacuum is measured, the interspace is in vacuum.

By giving adhesiveness to one film substrate of the semiconductor device, e.g., a surface of the sealing substrate 303, it can be attached to an object whose pressure is to be measured. The sealing substrate 303 is made of a film and it is so thin that it can conduct the pressure change of the object to the semiconductor device 380 accurately.

Naturally, the sealing substrates 303 and 306 are so thin that a thin semiconductor device having high flexibility can be provided.

Embodiment Mode 8

Embodiment Mode 8 will describe an example in which a semiconductor device having a piezoelectric element described in the above embodiment mode is applied as a pressure sensor. In this embodiment mode, a semiconductor device functioning as a sensor is applied to a pressure sensor of a system which monitors air pressure of tires.

Figure 10:
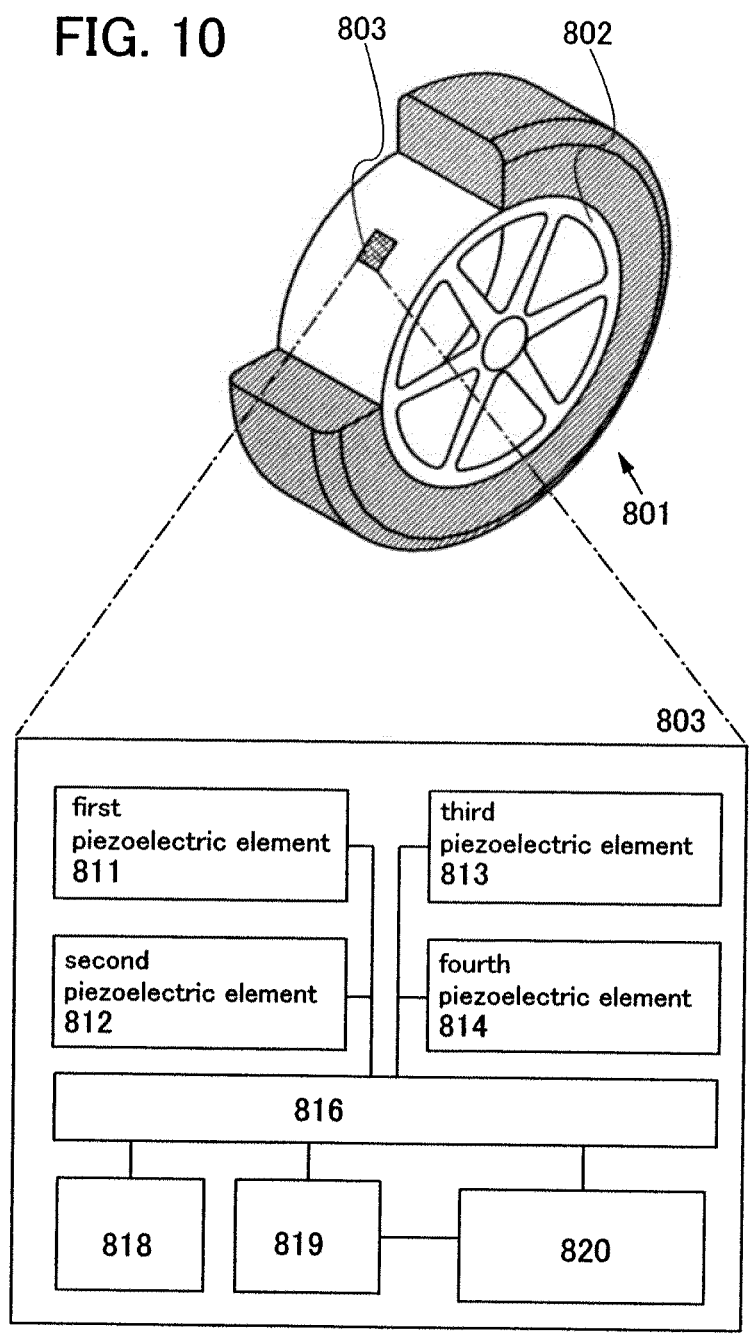
FIG. 10 shows an example of a pressure sensor according to one aspect of the present invention

As shown in FIG. 10, a semiconductor device 803 is disposed in a tire 801 with a wheel 802. The semiconductor device 803 may be provided inside the tire 801; however, since the tire may be broken, it is preferably attached to a valve part of the wheel. The semiconductor device 803 includes a plurality of piezoelectric elements and a control circuit which controls the plurality of piezoelectric elements. In this embodiment mode, the semiconductor device 803 includes four piezoelectric elements, i.e., first to fourth piezoelectric elements 811 to 814, and a control circuit 816 which controls the piezoelectric elements. Note that the number of the piezoelectric elements is not limited to four, and a plurality of piezoelectric elements may be provided. The first to fourth piezoelectric elements 811 to 814 may have a different sensitivity from each other. For example, by using piezoelectric elements having different detection areas, a piezoelectric element which can measure a low pressure band and a piezoelectric element which can measure a high pressure band are provided so as to achieve a wide measurement band. In addition, any one of the piezoelectric elements is used as a reference element.

By using the semiconductor device 803 like this, a pressure change can be obtained as a volume change and thus, change of a tire pressure can be checked. As a result, a tire can be prevented from being punctured etc., because of a reduced pressure of the tire. A pressure sensor of this embodiment mode can directly measure an air pressure of a tire, and thus, measurement accuracy can be increased.

In addition, in order to obtain information from the semiconductor device 803, a reader/writer device may be disposed in a car. The semiconductor device 803 obtains driving power from an electromagnetic wave emitted from the reader/writer, and conduct transmission and reception of information with the reader/writer through the electromagnetic wave. Thus, the semiconductor device 803 includes an electric circuit for wireless communication as shown in the above-described embodiment modes. For example, the semiconductor device includes an antenna 818, a memory 819 and a CPU (central processing unit) 820. Naturally, an inner battery may be incorporated in the semiconductor device 803.

By incorporating a pressure sensor of this embodiment mode, a tire pressure can be monitored relatively easily on a daily basis, without going to a car maintenance shop such as a service station.

A temperature sensor may be included in addition to the pressure sensor. By using both the pressure sensor and the temperature sensor, accuracy of tire pressure monitoring can be increased.

By using a semiconductor device of the present invention, a sensor having a new structure can be provided.

Embodiment Mode 9

Embodiment Mode 9 will describe a mode of a semiconductor device which measures pulse with a micro electro mechanical system.

A micro electro mechanical system of the present invention is extremely thin, and can be covered with a film substrate. Thus, the micro electro mechanical system is extremely flexible, and can be attached to a curved surface, for example, can be wrapped around a surface of a biologic body or a human body.

Figure 11:
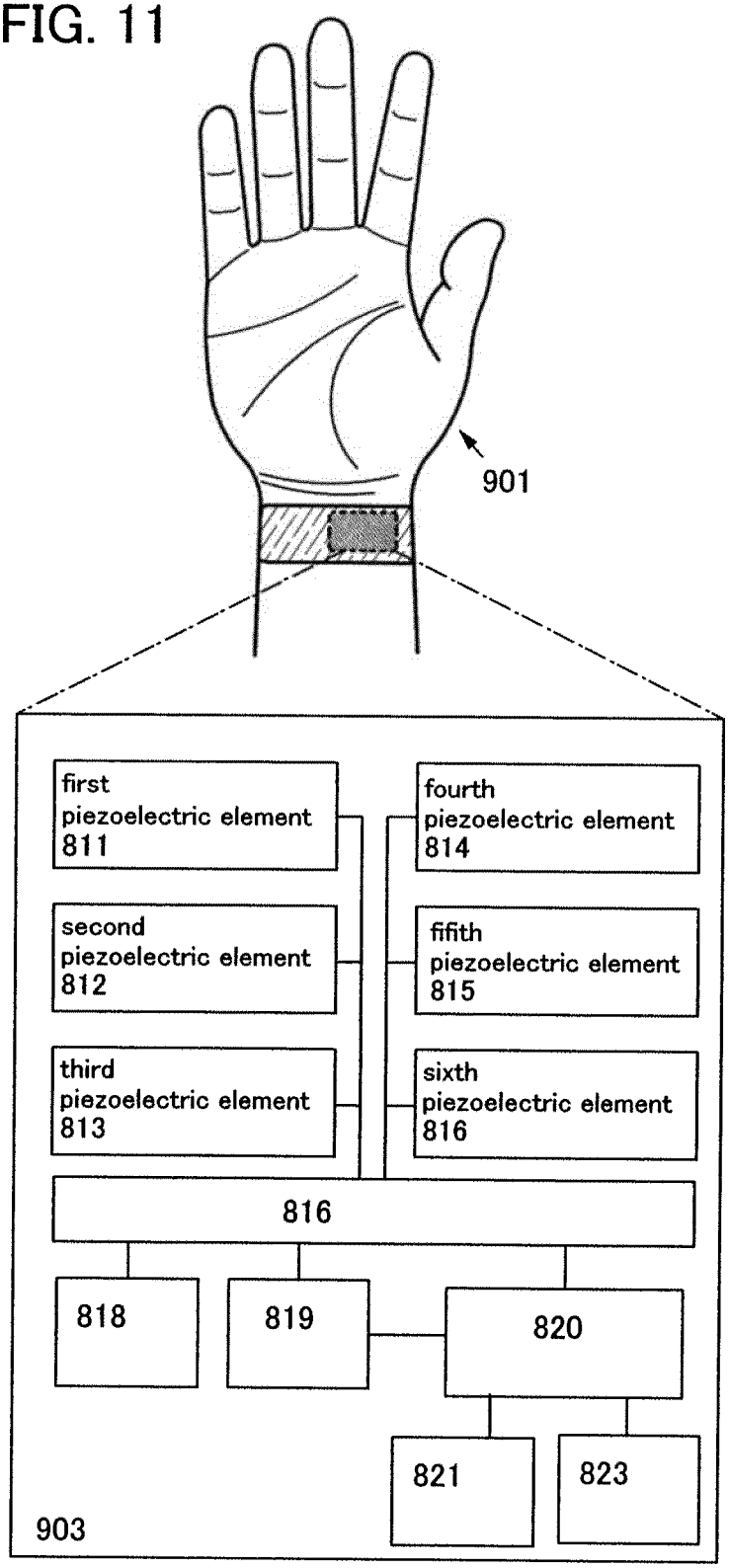
FIG. 11 shows an example of a pressure sensor according to one aspect of the present invention.

FIG. 11 shows an example in which the semiconductor device 903 is attached to a wrist 901. In this embodiment mode, pulse is measured with the semiconductor device 903 including six piezoelectric elements, i.e., first to sixth piezoelectric elements 811 to 816. Note that the number of piezoelectric elements is not limited to six, and a large number of piezoelectric elements may be provided. When a plurality of piezoelectric elements are provided in this manner, information of a piezoelectric element among the plurality of piezoelectric elements, which counts a maximum number of pulses, is output. By providing the plurality of piezoelectric elements in this manner, count errors of pulse can be reduced.

Figure 12A:
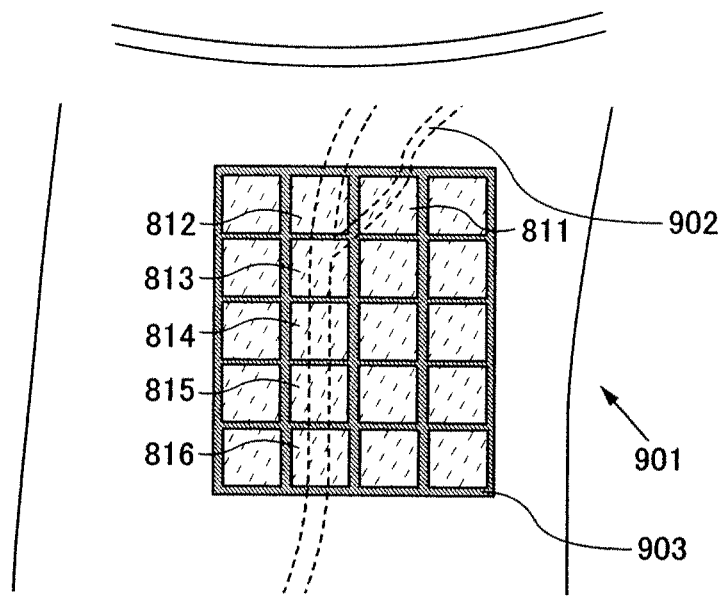
FIGS. 12A and 12B are each an enlarged view of a pressure sensor according to one aspect of the present invention.

The semiconductor device has a measurement face having a predetermined size and a large number of piezoelectric elements having a smaller area may be arranged in array in the measurement face. As shown in FIG. 12A, for example, the semiconductor device 903 in which 5×4 piezoelectric elements are arranged in array is attached to the wrist 901. At this time, piezoelectric elements which are arranged so as to check pulse of a blood vessel 902 are referred to as the first to sixth piezoelectric elements 811 to 816.

Figure 12B:
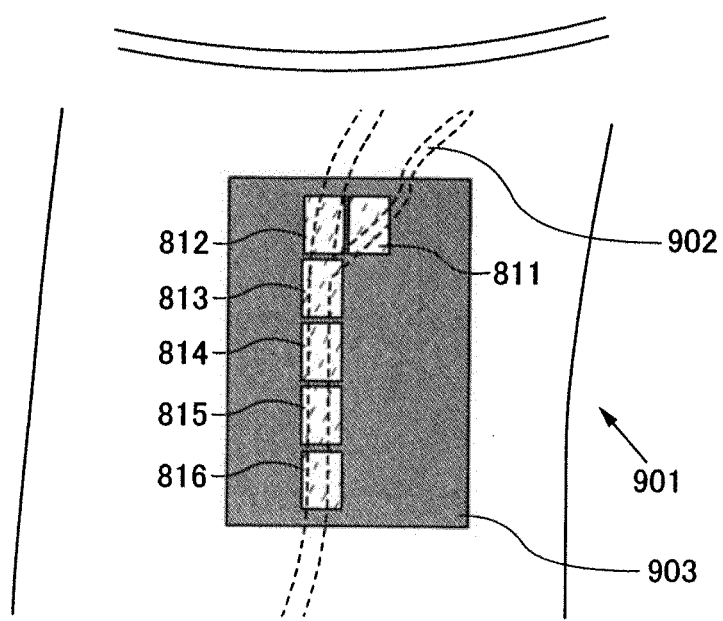

In addition, a piezoelectric element having a certain degree of area may be provided. The number of piezoelectric elements to be provided becomes smaller in accordance with the area of the piezoelectric elements. As shown in FIG. 12B, for example, the piezoelectric element may have a width which is almost equal to a width of the blood vessel, and the first to sixth piezoelectric elements 811 to 816 may be arranged along the blood vessel.

Further, the semiconductor device 903 can conduct wireless communication by having such an electric circuit as the above-described embodiment modes. For example, the semiconductor device 903 includes an antenna 818, a memory 819 and a CPU 820. The semiconductor device 903 may also include an input portion 821 and a display portion 823. A user can input his/her information to the input portion 821 and obtain information from the display portion 823. For example, based on measured pulse, advice or information on health can be displayed on the display portion 823.

Moreover, in the case of measuring pulse while exercising, calorie consumption can be calculated from the change of pulse or the like and shown. Additionally, while exercising, when more pulses than a desired level is shown, an alarm may be sounded.

By using a semiconductor device of the present invention, a sensor having a new structure can be provided.

This application is based on Japanese Patent application No. 2005-302343 filed on Oct. 17, 2005 with the Japanese Patent Office, the entire contents of which are hereby incorporated by reference.

What is claimed is:

1. A manufacturing method of a semiconductor device, comprising steps of:
    forming a peeling layer over a first substrate;
    forming a sensor on the peeling layer;
    forming a first spacer layer over the peeling layer and around the sensor;
    providing a film over the first spacer layer so as to form a first interspace defined by the first spacer layer, the peeling layer, and the film, the sensor being located in the first interspace;
    separating the first substrate from a set including the sensor, the film, and the first spacer layer;
    removing the peeling layer from the sensor; and
    attaching the set to a second substrate including an electric circuit and a second spacer layer formed over the electric circuit so that a second interspace, defined by the second spacer layer, the sensor, and the second substrate, is formed.

2. A manufacturing method of a semiconductor device according to claim 1, wherein the first spacer layer comprises at least one of acrylic resin, polyimide resin, melamine resin, polyester resin, polycarbonate resin, phenol resin, epoxy resin, polyacetal, polyether, polyurethane, polyamide, furan resin, and diallyl phthalate resin.

3. A manufacturing method of a semiconductor device according to claim 1, wherein the sensor is one of a piezoelectric element, a thermoelectric element, and a strain resistor element.

4. A manufacturing method of a semiconductor device according to claim 1, wherein each of the first interspace and the second interspace is filled with a rare gas or an inert gas.

5. A manufacturing method of a semiconductor device according to claim 1, wherein the peeling layer comprises at least one of tungsten, titanium, tantalum, molybdenum, neodymium, nickel, cobalt, zirconium, zinc, ruthenium, rhodium, osmium, and iridium.

6. A manufacturing method of a semiconductor device according to claim 1, wherein the second spacer layer is conductive.

7. A manufacturing method according to claim 1, wherein the first substrate is selected from a glass substrate, a quartz substrate, and a plastic substrate.

8. A manufacturing method of a semiconductor device according to claim 1, wherein the first spacer layer and the second spacer layer are put in direct contact with each other.

9. A manufacturing method of a semiconductor device, comprising steps of:
    forming a first peeling layer over a first substrate;
    forming a sensor on the first peeling layer;
    forming a first spacer layer over the first peeling layer and around the sensor;
    providing a film over the first spacer layer so as to form a first interspace defined by the first spacer layer, the first peeling layer, and the film, the sensor being located in the first interspace;
    separating the first substrate from a first set including the sensor, the film, and the first spacer layer;
    removing the first peeling layer from the sensor;
    attaching the first set to a second substrate, over which an electric circuit is formed with a second peeling layer interposed therebetween, using a second spacer layer made of an anisotropic conductive film so that the second spacer layer is on top and in direct contact with the electric circuit and the sensor, and a second interspace is formed, defined by the second spacer layer, the sensor, and the second substrate;
    separating the second substrate from a second set including the film, the first spacer layer, the sensor, the second spacer layer, and the electric circuit; and
    attaching a third substrate to the second set.

10. A manufacturing method of a semiconductor device according to claim 9, wherein the first spacer layer comprises at least one of acrylic resin, polyimide resin, melamine resin, polyester resin, polycarbonate resin, phenol resin, epoxy resin, polyacetal, polyether, polyurethane, polyamide, furan resin, and diallyl phthalate resin.

11. A manufacturing method of a semiconductor device according to claim 9, wherein the sensor is one of a piezoelectric element, a thermoelectric element, and a strain resistor element.

12. A manufacturing method of a semiconductor device according to claim 9, wherein each of the first interspace and the second interspace is filled with a rare gas or an inert gas.

13. A manufacturing method of a semiconductor device according to claim 9, wherein the first peeling layer and the second peeling layer comprise at least one of tungsten, titanium, tantalum, molybdenum, neodymium, nickel, cobalt, zirconium, zinc, ruthenium, rhodium, palladium, osmium, and iridium.

14. A manufacturing method according to claim 9, wherein the first substrate and the second substrate each are selected from a glass substrate, a quartz substrate, and a plastic substrate.

15. A manufacturing method of a semiconductor device according to claim 9, wherein the first spacer layer and the second spacer layer are put in direct contact with each other.

16. A manufacturing method of a semiconductor device, comprising steps of:
    forming a peeling layer over a base substrate;
    forming a functional layer on the peeling layer;
    forming a first spacer layer over the peeling layer and around the functional layer;
    providing a first substrate over the first spacer layer so as to form a first interspace defined by the functional layer, the peeling layer, and the first substrate, the functional layer being comprised in the first interspace;

separating the first substrate from a set including the first spacer layer, the functional layer, and the first substrate by using the peeling layer;

removing the peeling layer from the functional layer; and attaching the set to a second substrate on which a second spacer layer is formed so that a second interspace is formed, the second interspace being defined by the second spacer layer, the second substrate, and the functional layer.

17. A manufacturing method of a semiconductor device according to claim 16, wherein the second substrate comprises another functional layer.

18. A manufacturing method of a semiconductor device according to claim 16, wherein the functional layer comprises a pair of electrode and a piezoelectric layer.

19. A manufacturing method of a semiconductor device according to claim 16, wherein the first spacer layer and the second spacer layer are put in direct contact with each other.

* * * * *